US010664789B2

(12) United States Patent
Lau et al.

(10) Patent No.: US 10,664,789 B2
(45) Date of Patent: May 26, 2020

(54) METHOD AND SYSTEM FOR PERSONALIZED MEDICAL MONITORING AND NOTIFICATIONS THEREFOR

(71) Applicant: IpVenture, Inc., Los Altos, CA (US)

(72) Inventors: Chung Lau, Sunnyvale, CA (US); C. Douglass Thomas, Saratoga, CA (US)

(73) Assignee: IpVenture, Inc., San Jose, CA (US)

( * ) Notice: Subject to any disclaimer, the term of this patent is extended or adjusted under 35 U.S.C. 154(b) by 233 days.

(21) Appl. No.: 14/306,150

(22) Filed: Jun. 16, 2014

(65) Prior Publication Data

US 2014/0296659 A1  Oct. 2, 2014

Related U.S. Application Data

(62) Division of application No. 13/047,737, filed on Mar. 14, 2011, now Pat. No. 8,753,273, which is a division of application No. 10/397,641, filed on Mar. 26, 2003, now Pat. No. 7,905,832.

(60) Provisional application No. 60/444,198, filed on Jan. 30, 2003, provisional application No. 60/418,491, filed on Oct. 15, 2002, provisional application No. 60/404,645, filed on Aug. 19, 2002, provisional application No. 60/375,998, filed on Apr. 24, 2002.

(51) Int. Cl.
| | |
|---|---|
| A61B 5/00 | (2006.01) |
| A61B 5/02 | (2006.01) |
| A61B 5/04 | (2006.01) |
| A61B 5/11 | (2006.01) |
| H04W 4/02 | (2018.01) |
| H04W 4/20 | (2018.01) |
| G06F 11/30 | (2006.01) |
| G06F 19/00 | (2018.01) |
| G06Q 10/00 | (2012.01) |
| G06Q 10/08 | (2012.01) |
| G06Q 10/10 | (2012.01) |
| G06Q 50/22 | (2018.01) |
| G06Q 50/24 | (2012.01) |
| G16H 50/20 | (2018.01) |
| H04L 29/08 | (2006.01) |
| H04W 4/029 | (2018.01) |
| H04W 64/00 | (2009.01) |
| A61B 5/0205 | (2006.01) |

(52) U.S. Cl.
CPC ....... *G06Q 10/0833* (2013.01); *A61B 5/0002* (2013.01); *A61B 5/0022* (2013.01); *A61B 5/0024* (2013.01); *A61B 5/02055* (2013.01); *A61B 5/1112* (2013.01); *A61B 5/1123* (2013.01); *A61B 5/6801* (2013.01); *A61B 5/7282* (2013.01); *A61B 5/742* (2013.01); *G06F 11/3013* (2013.01); *G06F 11/3055* (2013.01); *G06F 11/3058* (2013.01); *G06F 19/34* (2013.01); *G06F 19/3418* (2013.01); *G06Q 10/00* (2013.01); *G06Q 10/0832* (2013.01); *G06Q 10/107* (2013.01); *G06Q 50/22* (2013.01); *G06Q 50/24* (2013.01); *G16H 50/20* (2018.01); *H04L 67/04* (2013.01); *H04L 67/18* (2013.01); *H04W 4/02* (2013.01); *H04W 4/029* (2018.02); *H04W 4/20* (2013.01); *A61B 5/02* (2013.01); *A61B 5/04* (2013.01); *A61B 5/1116* (2013.01); *A61B 5/1118* (2013.01); *H04W 4/027* (2013.01); *H04W 64/00* (2013.01); *Y10S 128/92* (2013.01)

(58) Field of Classification Search
CPC ....... A61B 5/74; A61B 5/7435; A61B 5/7465; A61B 5/0022; A61B 5/1112; A61B 5/1113; G01S 5/0231; G06F 19/3406; G06F 19/3418; G06F 19/3487
See application file for complete search history.

(56) References Cited

U.S. PATENT DOCUMENTS

| | | |
|---|---|---|
| 3,975,941 A | 8/1976 | Smith |
| 4,719,920 A | 1/1988 | Alt et al. |
| 5,115,223 A | 5/1992 | Moody |
| 5,337,579 A | 8/1994 | Saia, III et al. |
| 5,347,274 A | 9/1994 | Hassett |
| 5,353,034 A | 10/1994 | Sato et al. |
| 5,389,934 A | 2/1995 | Kass |
| 5,394,333 A | 2/1995 | Kao |
| 5,400,020 A | 3/1995 | Jones et al. |
| 5,422,816 A | 6/1995 | Sprague et al. |
| 5,461,365 A | 10/1995 | Schlager et al. |
| 5,470,233 A | 11/1995 | Fruchterman et al. |
| 5,491,486 A | 2/1996 | Welles, II et al. |

(Continued)

FOREIGN PATENT DOCUMENTS

| | | |
|---|---|---|
| EP | 0 874 529 A2 | 10/1998 |
| EP | 1 037 447 A2 | 9/2000 |

(Continued)

OTHER PUBLICATIONS

Capozza, P.T., et al. "A single-chip narrow-band frequency domain excisor for a Global Positioning System (GPS) receiver," IEEE Journal of Solid-State Circuits, vol. 35, Issue 3, Mar. 2000, pp. 401-411.

(Continued)

*Primary Examiner* — G Steven Vanni

(57) ABSTRACT

Improved methods and systems for personal medical monitoring are disclosed. The monitoring yields status information pertaining to persons being monitored. Notifications, recommendations and/or actions can be initiated by examination or analysis of the status information. The status information can include health, position (location) and other information.

26 Claims, 13 Drawing Sheets

(56) References Cited

U.S. PATENT DOCUMENTS

| | | |
|---|---|---|
| 5,512,902 A | 4/1996 | Guthrie et al. |
| 5,515,858 A | 5/1996 | Myllymaki |
| 5,528,247 A | 6/1996 | Nonami |
| 5,528,518 A | 6/1996 | Bradshaw et al. |
| 5,532,690 A | 7/1996 | Hertel |
| 5,539,748 A | 7/1996 | Raith |
| 5,541,845 A | 7/1996 | Klein |
| 5,543,789 A | 8/1996 | Behr et al. |
| 5,550,551 A | 8/1996 | Alesio |
| 5,563,606 A | 10/1996 | Wang |
| 5,568,119 A | 10/1996 | Schipper et al. |
| 5,570,412 A | 10/1996 | LeBlanc |
| 5,576,716 A | 11/1996 | Sadler |
| 5,592,173 A | 1/1997 | Lau et al. |
| 5,598,460 A | 1/1997 | Tendler |
| 5,604,708 A | 2/1997 | Helms et al. |
| 5,623,260 A | 4/1997 | Jones |
| 5,623,418 A | 4/1997 | Rostoker |
| 5,627,517 A | 5/1997 | Theimer et al. |
| 5,629,678 A | 5/1997 | Gargano et al. |
| 5,633,874 A | 5/1997 | Diachina et al. |
| 5,650,770 A | 7/1997 | Schlager et al. |
| 5,652,570 A | 7/1997 | Lepkofker |
| 5,673,692 A | 10/1997 | Schulze et al. |
| 5,686,888 A | 11/1997 | Welles, II et al. |
| 5,710,551 A | 1/1998 | Ridgeway |
| 5,712,619 A | 1/1998 | Simkin |
| 5,731,757 A | 3/1998 | Layson, Jr. |
| 5,731,788 A | 3/1998 | Reeds |
| 5,742,233 A | 4/1998 | Hoffman et al. |
| 5,751,245 A | 5/1998 | Janky et al. |
| 5,771,001 A | 6/1998 | Cobb |
| 5,771,455 A | 6/1998 | Kennedy, III et al. |
| 5,774,876 A | 6/1998 | Woolley et al. |
| 5,786,789 A | 7/1998 | Janky |
| 5,797,091 A | 8/1998 | Clise et al. |
| 5,806,018 A | 9/1998 | Smith et al. |
| 5,808,565 A | 9/1998 | Matta et al. |
| RE35,920 E | 10/1998 | Sorden et al. |
| 5,825,283 A | 10/1998 | Camhi |
| 5,826,195 A | 10/1998 | Westerlage et al. |
| 5,835,907 A | 11/1998 | Newman |
| 5,841,352 A | 11/1998 | Prakash |
| 5,844,862 A | 12/1998 | Cocatre-Zilgien |
| 5,850,196 A | 12/1998 | Mowers |
| 5,852,775 A | 12/1998 | Hidary |
| 5,861,841 A | 1/1999 | Gildea et al. |
| 5,883,594 A | 3/1999 | Lau |
| 5,889,770 A | 3/1999 | Jokiaho et al. |
| 5,892,454 A | 4/1999 | Schipper et al. |
| 5,894,266 A | 4/1999 | Wood, Jr. et al. |
| 5,902,347 A | 5/1999 | Backman et al. |
| 5,905,461 A | 5/1999 | Neher |
| 5,910,799 A | 6/1999 | Carpenter et al. |
| 5,913,078 A | 6/1999 | Kimura et al. |
| 5,917,433 A | 6/1999 | Keillor et al. |
| 5,918,180 A | 6/1999 | Dimino |
| 5,928,309 A | 7/1999 | Korver et al. |
| 5,938,721 A | 8/1999 | Dussell et al. |
| 5,948,040 A | 9/1999 | DeLorme et al. |
| 5,948,043 A | 9/1999 | Mathis |
| 5,950,125 A | 9/1999 | Buhrmann et al. |
| 5,959,575 A | 9/1999 | Abbott |
| 5,959,577 A | 9/1999 | Fan et al. |
| 5,963,130 A | 10/1999 | Schlager et al. |
| 5,982,285 A | 11/1999 | Bueche et al. |
| 5,982,807 A | 11/1999 | Snell |
| 5,983,108 A | 11/1999 | Kennedy, III et al. |
| 5,983,158 A | 11/1999 | Suzuki et al. |
| 5,991,690 A | 11/1999 | Murphy |
| 5,995,849 A | 11/1999 | Williams et al. |
| 6,002,363 A | 12/1999 | Krasner |
| 6,002,982 A | 12/1999 | Fry |
| 6,009,319 A | 12/1999 | Khullar et al. |
| 6,013,007 A | 1/2000 | Root et al. |
| 6,014,080 A | 1/2000 | Layson, Jr. |
| 6,014,090 A | 1/2000 | Rosen et al. |
| 6,018,704 A | 1/2000 | Kohli et al. |
| 6,023,241 A | 2/2000 | Clapper |
| 6,031,496 A | 2/2000 | Kuittinen |
| 6,032,051 A | 2/2000 | Hall et al. |
| 6,034,622 A | 3/2000 | Levine |
| 6,052,646 A | 4/2000 | Kirkhart et al. |
| 6,052,696 A | 4/2000 | Euler et al. |
| 6,054,928 A | 4/2000 | Lemelson et al. |
| 6,064,336 A | 5/2000 | Krasner |
| 6,067,018 A | 5/2000 | Skelton et al. |
| 6,067,044 A | 5/2000 | Whelan et al. |
| 6,072,396 A | 6/2000 | Gaukel |
| 6,078,290 A | 6/2000 | McBurney et al. |
| 6,083,248 A | 7/2000 | Thompson |
| 6,083,353 A | 7/2000 | Alexander |
| 6,085,090 A | 7/2000 | Yee et al. |
| 6,094,168 A | 7/2000 | Duffett-Smith et al. |
| 6,100,806 A | 8/2000 | Gaukel |
| 6,101,710 A | 8/2000 | Selinger et al. |
| 6,104,334 A | 8/2000 | Allport |
| 6,111,540 A | 8/2000 | Krasner |
| 6,115,595 A | 9/2000 | Rodal et al. |
| 6,121,921 A | 9/2000 | Ishigaki |
| 6,125,325 A | 9/2000 | Kohli et al. |
| 6,131,067 A | 10/2000 | Girerd et al. |
| 6,140,863 A | 10/2000 | Fujisawa |
| 6,140,957 A | 10/2000 | Wilson et al. |
| 6,141,570 A | 10/2000 | O'Neill, Jr. et al. |
| 6,144,303 A | 11/2000 | Federman |
| 6,148,280 A | 11/2000 | Kramer |
| 6,154,422 A | 11/2000 | Shinkawa et al. |
| 6,163,696 A | 12/2000 | Bi et al. |
| 6,169,902 B1 | 1/2001 | Kawamoto |
| 6,171,264 B1 | 1/2001 | Bader |
| 6,172,640 B1 | 1/2001 | Durst et al. |
| 6,175,616 B1 | 1/2001 | Light et al. |
| 6,198,390 B1 | 3/2001 | Schlager et al. |
| 6,198,431 B1 | 3/2001 | Gibson |
| 6,198,930 B1 | 3/2001 | Schipper |
| 6,199,045 B1 | 3/2001 | Giniger et al. |
| 6,204,807 B1 | 3/2001 | Odagiri et al. |
| 6,212,133 B1 | 4/2001 | McCoy et al. |
| 6,226,622 B1 | 5/2001 | Dabbiere |
| 6,231,519 B1 | 5/2001 | Blants et al. |
| 6,232,916 B1 | 5/2001 | Grillo et al. |
| 6,236,358 B1 | 5/2001 | Durst et al. |
| 6,238,337 B1 | 5/2001 | Kambhatla et al. |
| 6,243,039 B1 | 6/2001 | Elliot |
| 6,243,660 B1 | 6/2001 | Hsu et al. |
| 6,246,376 B1 | 6/2001 | Bork et al. |
| 6,252,543 B1 | 6/2001 | Camp |
| 6,252,544 B1 | 6/2001 | Hoffberg |
| 6,259,944 B1 | 7/2001 | Margulis et al. |
| 6,263,280 B1 | 7/2001 | Stingone, Jr. |
| 6,266,612 B1 | 7/2001 | Dussell et al. |
| 6,272,457 B1 | 8/2001 | Ford et al. |
| 6,278,936 B1 | 8/2001 | Jones |
| 6,281,797 B1 | 8/2001 | Forster |
| 6,282,362 B1 | 8/2001 | Murphy et al. |
| 6,282,495 B1 | 8/2001 | Kirkhart et al. |
| 6,285,314 B1 | 9/2001 | Nagatsuma et al. |
| 6,292,687 B1 | 9/2001 | Lowell et al. |
| 6,298,306 B1 | 10/2001 | Suarez et al. |
| 6,300,875 B1 | 10/2001 | Schafer |
| 6,302,844 B1 | 10/2001 | Walker et al. |
| 6,304,467 B1 | 10/2001 | Nebrigic |
| 6,314,308 B1 | 11/2001 | Sheynblat et al. |
| 6,315,719 B1 * | 11/2001 | Rode ............. A61B 5/1112 600/300 |
| 6,317,049 B1 | 11/2001 | Toubia et al. |
| 6,321,091 B1 | 11/2001 | Holland |
| 6,323,807 B1 | 11/2001 | Golding et al. |
| 6,324,213 B1 | 11/2001 | Harrison |
| 6,327,533 B1 | 12/2001 | Chou |
| 6,330,149 B1 | 12/2001 | Burrell |
| 6,331,817 B1 | 12/2001 | Goldberg |
| 6,331,825 B1 | 12/2001 | Ladner et al. |

(56) References Cited

U.S. PATENT DOCUMENTS

| | | | |
|---|---|---|---|
| 6,339,397 B1 | 1/2002 | Baker |
| 6,340,928 B1 | 1/2002 | McCurdy |
| 6,342,847 B1 | 1/2002 | Archuleta et al. |
| 6,349,257 B1 | 2/2002 | Liu et al. |
| 6,353,390 B1 | 3/2002 | Beri et al. |
| 6,353,798 B1 | 3/2002 | Green et al. |
| 6,356,836 B1 | 3/2002 | Adolph |
| 6,356,841 B1 | 3/2002 | Hamrick et al. |
| 6,362,778 B2 | 3/2002 | Neher |
| 6,363,254 B1 | 3/2002 | Jones et al. |
| 6,363,323 B1 | 3/2002 | Jones |
| 6,366,871 B1* | 4/2002 | Geva ............... A61B 5/0002 340/539.12 |
| 6,373,430 B1 | 4/2002 | Beason et al. |
| 6,377,810 B1 | 4/2002 | Geiger et al. |
| 6,384,724 B1 | 5/2002 | Landais |
| 6,388,612 B1 | 5/2002 | Neher |
| 6,393,346 B1 | 5/2002 | Keith et al. |
| 6,404,352 B1 | 6/2002 | Ichikawa et al. |
| 6,407,698 B1 | 6/2002 | Ayed |
| 6,411,892 B1 | 6/2002 | Van Diggelen |
| 6,411,899 B2 | 6/2002 | Dussell et al. |
| 6,421,538 B1 | 7/2002 | Byrne |
| 6,426,719 B1 | 7/2002 | Nagareda et al. |
| 6,427,120 B1 | 7/2002 | Garin et al. |
| 6,430,602 B1 | 8/2002 | Kay et al. |
| 6,433,732 B1 | 8/2002 | Dutta et al. |
| 6,434,396 B1 | 8/2002 | Rune |
| 6,437,692 B1 | 8/2002 | Petite et al. |
| 6,441,778 B1 | 8/2002 | Durst et al. |
| 6,442,380 B1 | 8/2002 | Mohindra |
| 6,442,391 B1 | 8/2002 | Johansson et al. |
| 6,443,890 B1 | 9/2002 | Schulze et al. |
| 6,445,937 B1 | 9/2002 | daSilva |
| 6,453,237 B1 | 9/2002 | Fuchs et al. |
| 6,463,272 B1 | 10/2002 | Wallace et al. |
| 6,466,821 B1 | 10/2002 | Pianca et al. |
| 6,469,639 B2 | 10/2002 | Tanenhaus et al. |
| 6,471,087 B1 | 10/2002 | Shusterman |
| 6,478,736 B1 | 11/2002 | Mault |
| 6,484,034 B1 | 11/2002 | Tsunehara et al. |
| 6,496,775 B2 | 12/2002 | McDonald, Jr. et al. |
| 6,501,429 B2 | 12/2002 | Nakamura et al. |
| 6,505,048 B1 | 1/2003 | Moles et al. |
| 6,505,049 B1 | 1/2003 | Dorenbosch |
| 6,512,456 B1* | 1/2003 | Taylor, Jr. ............ A61B 5/1112 340/539.1 |
| 6,513,532 B2 | 2/2003 | Mault et al. |
| 6,522,871 B1 | 2/2003 | Patrick et al. |
| 6,522,889 B1 | 2/2003 | Aarnio |
| 6,529,164 B1 | 3/2003 | Carter |
| 6,529,822 B1 | 3/2003 | Millington et al. |
| 6,544,193 B2 | 4/2003 | Abreu |
| 6,552,652 B2 | 4/2003 | Beken |
| 6,553,336 B1 | 4/2003 | Johnson et al. |
| 6,559,620 B2 | 5/2003 | Zhou et al. |
| 6,560,463 B1 | 5/2003 | Santhoff |
| 6,569,094 B2 | 5/2003 | Suzuki et al. |
| 6,571,193 B1 | 5/2003 | Unuma et al. |
| 6,579,231 B1* | 6/2003 | Phipps ................ A61B 5/0002 128/903 |
| 6,579,844 B1 | 6/2003 | Morrison et al. |
| 6,611,688 B1 | 8/2003 | Raith |
| 6,616,593 B1 | 9/2003 | Elliott et al. |
| 6,625,437 B1 | 9/2003 | Jampolsky et al. |
| 6,630,885 B2 | 10/2003 | Hardman et al. |
| 6,640,085 B1 | 10/2003 | Chatzipetros et al. |
| 6,650,907 B1 | 11/2003 | Kamperschroer et al. |
| 6,661,372 B1 | 12/2003 | Girerd et al. |
| 6,679,071 B1 | 1/2004 | Storey et al. |
| 6,696,982 B2 | 2/2004 | Yoshioka et al. |
| 6,697,103 B1 | 2/2004 | Fernandez et al. |
| 6,697,730 B2 | 2/2004 | Dickerson |
| 6,714,158 B1 | 3/2004 | Underbrink et al. |
| 6,714,791 B2 | 3/2004 | Friedman |
| 6,721,542 B1 | 4/2004 | Anttila et al. |
| 6,741,927 B2 | 5/2004 | Jones |
| 6,747,675 B1 | 6/2004 | Abbott et al. |
| 6,748,318 B1 | 6/2004 | Jones |
| 6,788,766 B2 | 9/2004 | Logan |
| 6,801,853 B2 | 10/2004 | Workman |
| 6,804,606 B2 | 10/2004 | Jones |
| 6,825,767 B2* | 11/2004 | Humbard ............ G08B 21/0202 340/573.1 |
| 6,832,093 B1 | 12/2004 | Ranta |
| 6,847,892 B2 | 1/2005 | Zhou et al. |
| 6,856,804 B1 | 2/2005 | Ciotta |
| 6,856,807 B1 | 2/2005 | Raith |
| 6,865,385 B1 | 3/2005 | Kohda et al. |
| 6,876,862 B1 | 4/2005 | Tanaka |
| 6,888,879 B1 | 5/2005 | Lennen |
| 6,937,900 B1 | 8/2005 | Pianca et al. |
| 6,952,645 B1 | 10/2005 | Jones |
| 6,975,941 B1 | 12/2005 | Lau et al. |
| 6,980,813 B2 | 12/2005 | Mohi et al. |
| 6,980,826 B2 | 12/2005 | Yamaguchi |
| 6,997,882 B1 | 2/2006 | Parker et al. |
| 7,010,144 B1 | 3/2006 | Davis et al. |
| 7,071,842 B1 | 7/2006 | Brady, Jr. |
| 7,085,253 B2 | 8/2006 | Yang |
| 7,110,773 B1 | 9/2006 | Wallace et al. |
| 7,136,832 B2 | 11/2006 | Li et al. |
| 7,187,278 B2 | 3/2007 | Biffar |
| 7,212,829 B1 | 5/2007 | Lau et al. |
| 7,218,938 B1 | 5/2007 | Lau et al. |
| 7,253,731 B2 | 8/2007 | Joao |
| 7,308,272 B1 | 12/2007 | Wortham |
| 7,321,774 B1 | 1/2008 | Lau et al. |
| 7,325,061 B2 | 1/2008 | Haruki |
| 7,366,522 B2 | 4/2008 | Thomas |
| 7,375,682 B1 | 5/2008 | Tester et al. |
| 7,403,972 B1 | 7/2008 | Lau et al. |
| 7,482,920 B2 | 1/2009 | Joao |
| 7,539,557 B2 | 5/2009 | Yamauchi |
| 7,809,377 B1 | 10/2010 | Lau et al. |
| 7,905,832 B1 | 3/2011 | Lau et al. |
| 7,953,809 B2 | 5/2011 | Lau et al. |
| 8,176,135 B2 | 5/2012 | Lau et al. |
| 8,285,484 B1 | 10/2012 | Lau et al. |
| 8,301,158 B1 | 10/2012 | Thomas |
| 8,447,822 B2 | 5/2013 | Lau et al. |
| 8,611,920 B2 | 12/2013 | Lau et al. |
| 8,620,343 B1 | 12/2013 | Lau et al. |
| 8,700,050 B1 | 4/2014 | Thomas |
| 8,725,165 B2 | 5/2014 | Lau et al. |
| 8,753,273 B1 | 6/2014 | Lau et al. |
| 8,868,103 B2 | 10/2014 | Thomas |
| 8,886,220 B2 | 11/2014 | Lau et al. |
| 8,975,941 B2 | 3/2015 | Zierhofer |
| 9,049,571 B2 | 6/2015 | Lau et al. |
| 9,074,903 B1 | 7/2015 | Lau et al. |
| 9,182,238 B2 | 11/2015 | Lau et al. |
| 9,219,988 B2 | 12/2015 | Lau et al. |
| 9,456,350 B2 | 9/2016 | Lau et al. |
| 9,596,579 B2 | 3/2017 | Lau et al. |
| 9,706,374 B2 | 7/2017 | Lau et al. |
| 7,212,829 C1 | 8/2017 | Lau et al. |
| 9,723,442 B2 | 8/2017 | Lau et al. |
| 9,759,817 B2 | 9/2017 | Lau et al. |
| 9,769,630 B2 | 9/2017 | Lau et al. |
| 9,930,503 B2 | 3/2018 | Lau et al. |
| 9,998,886 B2 | 6/2018 | Lau et al. |
| 10,034,150 B2 | 7/2018 | Lau et al. |
| 10,327,115 B2 | 6/2019 | Lau et al. |
| 2001/0006891 A1 | 7/2001 | Cho |
| 2001/0020204 A1 | 9/2001 | Runyon et al. |
| 2001/0027378 A1 | 10/2001 | Tennison et al. |
| 2001/0027384 A1* | 10/2001 | Schulze ............... A61B 5/0006 702/188 |
| 2001/0027525 A1 | 10/2001 | Gamlin |
| 2001/0028304 A1 | 10/2001 | I'Anson et al. |
| 2001/0041554 A1 | 11/2001 | Rowell |
| 2001/0044299 A1 | 11/2001 | Sandegren |
| 2001/0044332 A1 | 11/2001 | Yamada et al. |

(56) References Cited

U.S. PATENT DOCUMENTS

| | | |
|---|---|---|
| 2001/0047125 A1 | 11/2001 | Quy |
| 2001/0052849 A1 | 12/2001 | Jones, Jr. |
| 2002/0000916 A1 | 1/2002 | Richards |
| 2002/0000930 A1 | 1/2002 | Crowson et al. |
| 2002/0008661 A1 | 1/2002 | McCall et al. |
| 2002/0015439 A1 | 2/2002 | Kohli et al. |
| 2002/0016173 A1 | 2/2002 | Hunzinger |
| 2002/0027507 A1 | 3/2002 | Yarin et al. |
| 2002/0028988 A1 | 3/2002 | Suzuki et al. |
| 2002/0036593 A1 | 3/2002 | Ying |
| 2002/0038182 A1 | 3/2002 | Wong et al. |
| 2002/0049742 A1 | 4/2002 | Chan et al. |
| 2002/0050945 A1 | 5/2002 | Tsukishima et al. |
| 2002/0055362 A1 | 5/2002 | Aoyama |
| 2002/0057192 A1 | 5/2002 | Eagleson et al. |
| 2002/0063622 A1 | 5/2002 | Armstrong et al. |
| 2002/0071677 A1 | 6/2002 | Sumanaweera |
| 2002/0077080 A1 | 6/2002 | Greene |
| 2002/0087260 A1 | 7/2002 | Hancock et al. |
| 2002/0087619 A1 | 7/2002 | Tripathi |
| 2002/0094067 A1 | 7/2002 | August |
| 2002/0099567 A1 | 7/2002 | Joao |
| 2002/0111171 A1 | 8/2002 | Boesch et al. |
| 2002/0111819 A1 | 8/2002 | Li et al. |
| 2002/0115450 A1 | 8/2002 | Muramatsu |
| 2002/0115453 A1 | 8/2002 | Poulin et al. |
| 2002/0116080 A1 | 8/2002 | Birnbach et al. |
| 2002/0119770 A1 | 8/2002 | Twitchell et al. |
| 2002/0119789 A1 | 8/2002 | Friedman |
| 2002/0120475 A1 | 8/2002 | Morimoto |
| 2002/0120503 A1 | 8/2002 | Iwayama et al. |
| 2002/0138196 A1 | 9/2002 | Polidi et al. |
| 2002/0140081 A1 | 10/2002 | Chou et al. |
| 2002/0173910 A1 | 11/2002 | McCall et al. |
| 2002/0191757 A1 | 12/2002 | Belrose |
| 2002/0193121 A1 | 12/2002 | Nowak et al. |
| 2002/0193996 A1 | 12/2002 | Squibbs et al. |
| 2002/0198003 A1 | 12/2002 | Kaplan |
| 2002/0198055 A1 | 12/2002 | Bull et al. |
| 2003/0003943 A1 | 1/2003 | Bajikar |
| 2003/0009410 A1 | 1/2003 | Ramankutty et al. |
| 2003/0013445 A1 | 1/2003 | Fujiwara et al. |
| 2003/0018430 A1 | 1/2003 | Ladetto et al. |
| 2003/0036389 A1 | 2/2003 | Yen |
| 2003/0036683 A1* | 2/2003 | Kehr ............... G06F 19/325 600/300 |
| 2003/0054827 A1 | 3/2003 | Schmidl et al. |
| 2003/0068605 A1 | 4/2003 | Kullok et al. |
| 2003/0069759 A1 | 4/2003 | Smith |
| 2003/0083011 A1 | 5/2003 | Haller et al. |
| 2003/0083046 A1 | 5/2003 | Mathis |
| 2003/0083814 A1 | 5/2003 | Gronemeyer |
| 2003/0095540 A1 | 5/2003 | Mulligan et al. |
| 2003/0100326 A1 | 5/2003 | Grube et al. |
| 2003/0107514 A1 | 6/2003 | Syrjarinne et al. |
| 2003/0114206 A1 | 6/2003 | Timothy et al. |
| 2003/0151507 A1 | 8/2003 | Andre et al. |
| 2003/0163287 A1 | 8/2003 | Vock et al. |
| 2003/0182052 A1 | 9/2003 | DeLorme |
| 2003/0204132 A1 | 10/2003 | Suzuki et al. |
| 2004/0034470 A1 | 2/2004 | Workman |
| 2004/0046637 A1 | 3/2004 | Wesby Van Swaay |
| 2004/0114731 A1 | 6/2004 | Gillett et al. |
| 2004/0117108 A1 | 6/2004 | Nemeth |
| 2004/0192352 A1 | 9/2004 | Vallstrom et al. |
| 2004/0204820 A1 | 10/2004 | Diaz |
| 2004/0233065 A1 | 11/2004 | Freeman |
| 2005/0250440 A1 | 11/2005 | Zhou et al. |
| 2006/0173444 A1 | 8/2006 | Choy et al. |
| 2007/0156286 A1 | 7/2007 | Yamauchi |
| 2008/0021645 A1 | 1/2008 | Lau et al. |
| 2008/0261636 A1 | 10/2008 | Lau et al. |
| 2009/0042540 A1 | 2/2009 | Bodnar et al. |
| 2011/0022533 A1 | 1/2011 | Lau et al. |
| 2011/0223884 A1 | 9/2011 | Lau et al. |
| 2012/0220266 A1 | 8/2012 | Lau et al. |
| 2013/0203388 A1 | 8/2013 | Thomas et al. |
| 2013/0297524 A1 | 11/2013 | Lau et al. |
| 2014/0011524 A1 | 1/2014 | Lau et al. |
| 2014/0067708 A1 | 3/2014 | Lau et al. |
| 2014/0273953 A1 | 9/2014 | Lau et al. |
| 2014/0278084 A1 | 9/2014 | Lau et al. |
| 2014/0296659 A1 | 10/2014 | Lau et al. |
| 2015/0011243 A1 | 1/2015 | Thomas et al. |
| 2015/0038168 A1 | 2/2015 | Thomas et al. |
| 2015/0264576 A1 | 9/2015 | Lau et al. |
| 2016/0025863 A1 | 1/2016 | Lau et al. |
| 2016/0029175 A1 | 1/2016 | Lau et al. |
| 2016/0050533 A1 | 2/2016 | Lau et al. |
| 2016/0264576 A1 | 9/2016 | Yamamoto et al. |
| 2017/0013426 A1 | 1/2017 | Lau et al. |
| 2017/0094458 A1 | 3/2017 | Thomas et al. |
| 2017/0111776 A1 | 4/2017 | Lau et al. |
| 2017/0111777 A1 | 4/2017 | Lau et al. |
| 2017/0188208 A1 | 6/2017 | Lau et al. |
| 2017/0295462 A1 | 10/2017 | Lau et al. |
| 2017/0353841 A1 | 12/2017 | Lau et al. |
| 2018/0011201 A1 | 1/2018 | Lau et al. |
| 2018/0027394 A1 | 1/2018 | Lau et al. |
| 2018/0211216 A1 | 7/2018 | Lau et al. |
| 2018/0213372 A1 | 7/2018 | Lau et al. |
| 2018/0255439 A1 | 9/2018 | Lau et al. |
| 2018/0302759 A1 | 10/2018 | Lau et al. |
| 2019/0215643 A1 | 7/2019 | Lau et al. |

FOREIGN PATENT DOCUMENTS

| | | |
|---|---|---|
| EP | 1 037 447 A3 | 10/2001 |
| JP | 09251069 A | 9/1997 |
| JP | 11-64482 | 3/1999 |
| JP | 11-258325 | 9/1999 |
| JP | 11-289574 | 10/1999 |
| JP | 11-306491 | 11/1999 |
| JP | 2001344678 A | 12/2001 |
| WO | WO 97/14054 | 4/1997 |
| WO | WO 97/41654 A1 | 11/1997 |
| WO | WO 98/01769 A1 | 1/1998 |
| WO | WO 98/16045 A1 | 4/1998 |
| WO | WO 98/40837 | 9/1998 |
| WO | WO 00/51391 | 8/2000 |
| WO | WO 01/50151 A1 | 7/2001 |
| WO | WO 01/63318 A1 | 8/2001 |
| WO | WO 01/75700 A2 | 10/2001 |
| WO | WO 02/42979 A1 | 5/2002 |
| WO | WO 02/084618 A1 | 10/2002 |
| WO | WO 03/012720 A1 | 2/2003 |

OTHER PUBLICATIONS

"Introduction to SMS," by C. Tull of AnywhereYouGo.com, pp. 1-4 (downloaded:www.devx.com/wireless/articles/SMS/SMSintro-asp), Aug. 10, 2002.
Office Action for U.S. Appl. No. 10/397,641, dated Jul. 28, 2005.
Restriction Requirement for U.S. Appl. No. 10/397,641, dated Apr. 4, 2006.
Office Action for U.S. Appl. No. 10/397,641, dated Oct. 20, 2006.
Final Office Action for U.S. Appl. No. 10/397,641, dated Apr. 19, 2007.
Advisory Action for U.S. Appl. No. 10/397,641, dated Jun. 20, 2007.
Office Action for U.S. Appl. No. 10/397,641, dated Sep. 7, 2007.
Office Action for U.S. Appl. No. 10/397,641, dated Jun. 12, 2008.
Final Office Action for U.S. Appl. No. 10/397,641, dated Dec. 24, 2008.
Advisory Action for U.S. Appl. No. 10/397,641, dated Apr. 15, 2009.
Office Action for U.S. Appl. No. 10/397,641, dated Sep. 9, 2009.
Office Action for U.S. Appl. No. 10/397,641, dated May 26, 2010.
Notice of Allowance for U.S. Appl. No. 10/397,641, dated Nov. 12, 2010.
Restriction Requirement for U.S. Appl. No. 13/047,737, dated Jul. 25, 2011.

(56) References Cited

OTHER PUBLICATIONS

Office Action for U.S. Appl. No. 13/047,737, dated Sep. 27, 2011.
Office Action for U.S. Appl. No. 13/047,737, dated Mar. 14, 2011.
Office Action for U.S. Appl. No. 13/047,737, dated Apr. 12, 2012.
Advisory Action for U.S. Appl. No. 13/047,737, dated Jul. 6, 2012.
Office Action for U.S. Appl. No. 13/047,737, dated May 21, 2013.
Notice of Allowance for U.S. Appl. No. 13/047,737, dated Oct. 3, 2013.
Notice of Allowance for U.S. Appl. No. 13/047,737, dated Jan. 24, 2014.
"352C22 Miniature Low Profile ICP Accelerometer," Precision Accelerometers, PCB Piezoelectronics Products—SVS Division, webpages, pp. 1-2 (downloaded Apr. 11, 2002: www.pcb.com/products/svs/svs352c22.html).
"3G Mobile Internet Revolution, . . . only with Location Based Services!" pp. 1, (downloaded Aug. 10, 2002: http://webhome.idirect.com/~dental/3glocator/home.htm).
"Airline Cargo Containers," Case Study, RJI Incorporated, webpages, pp. 1-2 (downloaded Mar. 16, 2002: www.rji.cc/casestudies/airlinecargocontainers.html).
"Airline Food Carts," Case Study, RJI Incorporated, webpages, pp. 1-2 (downloaded Mar. 16, 2002: www.rji.cc/casestudies/airlinefoodcarts.html).
"Carrier and end-user applications for wireless location systems," TruePosition, Inc., http://www.trueposition.com/spie_app.htm, downloaded, Jul. 30, 2000, pp. 1-7.
"Devices for Text Messages in Deutsche Telekom's fixed network have already found their way into many households," Deutsche Telekom AG, Press Release, Mar. 13, 2002, pp. 1-2.
"Digital/Analog Compass Sensors" and "1655 Digital Compass Sensor," webpages, The Robson Company, Inc., pp. 1-2 (downloaded Apr. 11, 2002: www.dinsmoresensors.com/index.html).
"Enhanced Tracking," United Parcel Service of America, Inc. (UPS), webpages, pp. 1-2 (downloaded Jun. 1, 2002: www.ups.com/myupsinfo/info/etrack?pnav=stdservice).
"Fleet Management Systems-Asset Tracking Devices," Axiom Navigation Inc., 2000-2001 (downloaded Oct. 19, 2002: www.axiomnav.com/Prod_Systems/prod_system.asp).
"Frozen Food Warehouse," Case Study, RJI Incorporated, webpages, pp. 1-3 (downloaded Mar. 16, 2002: www.rji.cc/casestudies/frozenfoodwarehouse.html).
"FunMail Launches on the NTT DoCoMo i-mode network," FunMail, Press Release, May 2001, pp. 1-2.
"Global Locating Services," SkyBitz, webpage, p. 1, (downloaded Nov. 15, 2002: www.skybitz.com/services/gls.html).
"GLS Communicator," SkyBitz, webpages, pp. 1-2, (downloaded Nov. 15, 2002: www.skybitz.com/gls/communicator.html).
"Guide to Tracking Info.," Nippon Express, website page, p. 1 (downloaded Jun. 9, 2002: www.nittsu.co.jp/edoc/howtoe.htm).
"IO Data Develops GPS Adapter for I-Mode Mobile," AsiaBizTech, Sep. 17, 2002, pp. 1-2.
"Locate Networks: Our Service," Locate Networks, webpages, pp. 1-7 (downloaded Sep. 26, 2002: www.locatenetworks.com/).
"MMS phones: Don't believe the hype," CNN.com/SCI-TECH, Aug. 8, 2002, pp. 1-3.
"Mobile Location Based Services: Cell Tracking Devices of People & Thongs . . . ," pp. 1-2 (downloaded Aug. 10, 2002: http://3glocate.com).
"MoniTrack," Case Study, RJI Incorporated, webpages, pp. 1-2 (downloaded Mar. 16, 2002: www.rji.cc/technology/telematic.html).
"My ups.com Benefits," United Parcel Service of America, Inc. (UPS), webpage, p. 1 (downloaded Apr. 13, 2002: www.ups.com/myupsinfo/info/benefits?pnav=stdsservice).
"NavMate® Navigation System," Visteon Corporation, webpage, pp. 1-2 (downloaded Jun. 21, 2002: www.visteon.com/technology/automotive/navmate.html).
"News," SkyBitz, webpages, pp. 1-8, (downloaded Nov. 15, 2002: www.skybitz.com/about/news.html).
"Pakhound: Your Watchdog in the Shipping Industry," website pp., pp. 1-3 (downloaded Jun. 9, 2002: www.pakhound.com/fact.asp).
"pulver.com's Location Based Services Report," pulver.com, Inc., Oct. 2001, pp. 1-17 (downloaded Jun. 4, 2002: www.pulver.com/lbsreport/lastbsreport.02/oct01.txt).
"Radio Frequency Identification (RFID)," Case Study, RJI Incorporated, webpage, p. 1 (downloaded Mar. 16, 2002: www.rji.cc/technology/rfid.html).
"Real Time Location System (RTLS)," Case Study, RJI Incorporated, webpage, p. 1 (downloaded Mar. 16, 2002: www.rji.cc/technology/rtls.html).
"Real-Time Warehouse Tracking," Case Study, RJI Incorporated, webpages, pp. 1-2 (downloaded Mar. 16, 2002: www.rji.cc/casestudies/rtwarehousetracking.html).
"Savi Reusable Transport Container," Savi Technology, Inc., Apr. 30, 2002, pp. 1-2.
"Send images to i-mode phones," Mobile Media Japan, 2001, pp. 1-3.
"Ski Rental with Auto ID and Tracking," Case Study, RJI Incorporated, webpages, pp. 1-2 (downloaded Mar. 16, 2002: www.rji.cc/casestudies/skirentalcompany.html).
"Status Icons/Messages," Yahoo! Messenger Help, Yahoo! Inc., 2002, pp. 1-2.
"Technical Applications of Our Current Technology," Aetherwire, webpages, pp. 1-4 (downloaded Mar. 16, 2002: www.aetherwire.com/CDROM/General/appl1.html).
"Theme Park Visitors & Cashless Purchasing," Case Study, RJI Incorporated, webpages, pp. 1-2 (downloaded Mar. 16, 2002: www.rji.cc/casestudies/themepark.html).
"Track Shipments—Detailed Results," FedEx, webpages, pp. 1-2 (downloaded Oct. 29, 2002: www.fedex.com).
"Track Your FedEx Shipments via Email," FedEx, webpages, pp. 1-2 (downloaded Oct. 29, 2002: www.fedex.com).
"Tracking Helpful Tips," United Parcel Service of America, Inc. (UPS), webpages, pp. 1-2 (downloaded Jun. 1, 2002: www.ups.com/tracking/nm_help.html).
"Turning Position Into Knowledge," SkyBitz, webpage, p. 1, (downloaded Nov. 15, 2002: www.skybitz.com).
"UPS Package Tracking," United Parcel Service of America, Inc. (UPS), webpages, pp. 1- 2 (downloaded Apr. 13, 2002: www.ups.com/tracking/tracking.html).
"UPS Wireless Solutions," United Parcel Service of America, Inc. (UPS), webpage, p. 1 (downloaded Apr. 13, 2002: www.ups.com/myupsinfo/info/wireless?pnav=stdsservice).
"Welcome to Iship, Inc.," iShip, Inc., webpages, pp. 1-2, (downloaded Jun. 9, 2002: www.iship.com/).
"Welcome to Traker Systems," Tracker Systems, webpages, pp. 1-2 (downloaded Jun. 9, 2002: www.trakersystems.com).
"What are Instant Messages?" Yahoo! Messenger Help, Yahoo! Inc., 2002, pp. 1.
"What is "3G" technology?," CNN.com/SCI-TECH, Oct. 22, 2001, pp. 1-3.
"What is a Friend List?" Yahoo! Messenger Help, Yahoo! Inc., 2002, pp. 1.
"Wherify Wireless and SiRF Team to Deliver Child Locator System," Wherify Wireless, Inc., Press Release, Mar. 19, 2001, pp. 1-2.
"Wherify Wireless Breakthrough in Location-Based Services," Mobilemag.com, Feb. 28, 2001, p. 1.
"Wherify Wireless GPS Locator for Kids User Guide," Wherify Wireless, Inc., 2003, pp. 1-106.
"Wherify Wireless Location Services," Wherify Wireless, Inc., webpages, pp. 1-5 (downloaded: Mar. 25, 2003: www.wherifywireless.com/prod_watches.htm).
"Yahoo! Messenger—Sending Messages to a Mobile Phone," Yahoo! Messenger, Yahoo! Inc., 2002, pp. 1-7 (downloaded Oct. 27, 2002: http://messenger.yahoo.com/messenger/wireless/pc2sms/tour1.html(through /tour7.html)).
"Yahoo! Messenger for Text Messaging," Yahoo! Messenger, Yahoo! Inc., 2002, pp. 1-10 (downloaded Oct. 27, 2002: http://messenger.yahoo.com/messenger/wireless/smsmsgr/tour1.html (through /tour7.html)).

(56) References Cited

OTHER PUBLICATIONS

"Yahoo! Messenger for WAP," Yahoo Messenger, Yahoo! Inc., 2002 (tours 1-9), pp. 1-17 (downloaded Oct. 27, 2002: www.messenger.yahoo.com/messenger/wireless/wap/tour1.html(through /tour9.html)).
Accelerometers—General Purpose, LP Series, Crossbow Technology, Inc., data sheet, pp. 1-3 (downloaded Apr. 11, 2002: www.xbow.com/Products/Accelerometers.htm).
Bickers, "Eyes in the sky," SafeTzone Technology Corporation, webpages, 2001, pp. 1-3 (downloaded: www.safetzone.com/newsKiosk.asp).
Chertkoff, Rachel, "Vehicle Locator Systems," Pager Technology, pp. 1-2, 1998.
Crossbow Product Guide—Accelerometers, Crossbow Technology, Inc., webpages, pp. 1-3 (downloaded Apr. 11, 2002: www.xbow.com/Products/Accelerometers.htm).
Culler, D. et al., "MICA: The Commercialization of Microsensor Motes," Sensors (Apr. 1, 2002), pp. 1-5.
Darabi et al., "A 2.4-GHz CMOS Transceiver for Bluetooth," IEEE Journal of Solid-State Circuits, vol. 36, No. 12 (Dec. 2001), pp. 2016-2024.
F. Rivera, "Special Report: Keeping Tabs on Your Teen," 7 News, Boston, Apr. 30, 2002, pp. 1-3.
FedEx Insight, FedEx, webpages, pp. 1-11 (downloaded Oct. 29, 2002: www.fedex.com).
Fraden, J., Handbook of Modern Sensors: Physics, Designs and Applications, Second Edition, Springer-Verlag (1996), cover, pp. 310-354, 384-431, 458-493, and 513-528.
GPS2000, Omega Research and Development, Inc., webpages, pp. 1-9 (pp. 7-9 pertain to an online tour) (downloaded Jul., 14, 2003: www.gps2000online.com/).
Grimes, et al., "Wireless Magnetoelastic Resonance Sensors: A Critical Review," Sensors, vol. 2 (Jul. 23, 2002), pp. 294-313.
Helfenstein et al., Circuits and Systems for Wireless Communications, Kluwer Academic Publishers (2000), cover pages, pp. 3-7, 9-34, and 37-47.
Hill et al., "System Architecture Directions for Networked Sensors," ACM/ASPLOS-IX (Nov. 2000), 12 pages.
IMVironment, Yahoo! Messenger Yahoo! Inc., 2002, pp. 1-12 (downloaded (including) Oct. 27, 2002: http://help.yahoo.com/help/us/mesg/imv/imv-01.html(through /index5.html).
K. Hill "Prada Uses Smart Tags to Personalize Shopping," CRMDaily.com, Apr. 24, 2002, pp. 1-4.
Madou, Marc J., Fundamentals of Microfabrication: the Science of Miniaturization, Second Edition, CRC Press (2002) 139 pages.
LoadTrak, pp. 1-2 (downloaded Jun. 4, 2002: www.load-trak.com).
Mainwaring et al., "Wireless Sensor Networks for Habitat Monitoring," ACM (Sep. 28, 2002) pp. 88-97.
My.Roadway!, Roadway Express, Inc., webpages, pp. 1-2, (downloaded Jun. 9, 2002: www.quiktrak.roadway.com/cgi-bin/quiktrak).
Package, Dictionary.com, http://dictionary.reference.com/browse/package (last accessed Nov. 6, 2013), 3 pgs.
Packtrack™, PackTrack.com, webpages, pp. 1-2 (downloaded Jun. 9, 2002: www.packtrack.com).
Precision Accelerometers, PCB Piezoelectronics Products—SVS Division, webpages, pp. 1-2 (downloaded Apr. 11, 2002: www.pcb.com/products/svs/index.html).
Rabinowitz and Spilker, Jr., "A New Positioning System Using Television Synchronization Signals," Rosum Corporation, pp. 1-11 (downloaded May 21, 2003).
Razavi, Behzad, RF Microelectronics, Prentice Hall (1998), cover pages, pp. 1-10, and 118-297.
Rofougaran et al., "A Single-Chip 900-MHz Spread-Spectrum Wireless Transceiver in 1-µm CMOS—Part II: Receiver Design," IEEE Journal of Solid-State Circuits, vol. 33, No. 4 (Apr. 1998), pp. 535-547.
Senturia, Stephen D., Microsystem Design, Kluwer Academic Publishers (2001), cover pages, and pp. 3-14.
SiRF Debuts Revolutionary Architecture and Technologies to Further Drive GPS into the Mainstream, SiRF.com, Aug. 16, 1999 (archived Dec. 22, 1999), http://web.archive.org/web/19991222194810/http:/www.sirf.com/as_prss2_3.htm, 4 pgs.
Steyaert et al., "A 2-V CMOS Cellular Transceiver Front-End," IEEE Journal of Solid-State Circuits, vol. 35, No. 12, Dec. 2000, pp. 1895-1907.
PCVtrak™ Installation and Operator's Manual, Trimble Navigation, 24623-00 Rev. A, May 1994, pp. 1-259.
"Advanced Traveler Aid Systems for Public Transportation," Final Report, Federal Transit Administration, Sep. 1994, pp. 1-131.
Campbell, Laurel, "Security—Military satellite enlisted to thwart car crime," The Commercial Appeal, Sep. 26, 1996, pp. 5B.
Law, Alex, "Week in Wheels/ . . . From a Driver's Notebook," Newsday, Inc., Sep. 20, 1996, pp. C03.
Cortez, Angela, "Springs police can track thief, vehicles," The Denver Post, Sep. 10, 1996, pp. B-01.
"OnGuard Tracker Nabs Auto Burglar," Global Positioning & Navigation News, vol. 6, No. 16, Aug. 8, 1996.
Nauman, Matt, "Pressing the Panic Button: Car Security Enters a New Age with Cellular Phones and Satellites that Watch Over You," San Jose Mercury News, Jun. 21, 1996, pp. 1G.
"Monday Briefing" San Antonio Express-News, p. 1, Part B, Jun. 10, 1996.
Dominguez, Raul, "Women get their day in sun—American Golf planning events nationwide May 18," San Antonio Express-News, Apr. 18, 1996, pp. 2, part B.
"Business People Burnsy's Grill Names Two," Omaha World-Herald, Section Business, p. 4M, Oct. 20, 1996.
Dunkelberger, Lloyd, "Lawmakers question criminal-tracking system," Sarasota Herald-Tribune (Florida), pp. 16A, Nov. 28, 1999.
Powell, Barbara. "New gadgets help drivers find their way," Fort Worth Star-Telegram (Texas), p. 1, Jan. 20, 1997.
Brauer, David, "Satellite 'Big Brother' Tracks Ex-Inmates; Agencies Experiment with GPS to Monitor Parolee Whereabouts," Chicago Tribune, Section: News, p. 31, Dec. 18, 1998.
Prohaska, Thomas J, "Satellite Will Keep Tabs on Convicts," Buffalo News (New York), Section: Local, p. 5B, Sep. 20, 1999.
Dailey et al. "Automatic Transit Location System," Final Research Report, 55 pgs., Feb. 1996.
Maguire, Jr. et al. "SmartBadges: a wearable computer and communication system," codes/CASHE '98, 47 pgs., 1998.
Koshima et al. "Personal locator services emerge," IEEE Spectrum, Feb. 2000, pp. 41-48.
Sauer, Matthew, "Company Finds Niche by Giving Directions . . . " Sarasota Herald-Tribune (Florida), Section: Business Weekly, p. 1, Jul. 7, 1997.
Jackson, Terry, "Smart Cars Whether by Satellite or the Internet, High-Tech Devices and Services May Make Crumpled Road Maps a Thing of the Past," The Miami Herald, Section: Travel, p. 1J, Oct. 6, 1996.
"Money-Back Guarantee Policy" from fedex.com, Federal Express Corporation, 2000, 3 pgs.
"Audiovox Intros GPS, Bluetooth Phone;" INT Media Group, Inc. (allNetDevices), Apr. 5, 2002, 3 pgs.
"Danger—Products" and "Hiptop Communicator Brochure," Danger, Inc., 2000, 4 pgs.
"Developing a GPSs for the Global Supply Chain," Aberdeen Group, Inc., Executive White Paper, Jun. 2002, pp. 1-15.
"EarthTrak™ Vehicle Tracking Systems," Outfitter Satellite, Inc., 1998, 2 pgs.
"Global Cell Phone Location," Axiom Navigation Inc., 2001, 1 pg. (downloaded Oct. 19, 2002: www.axiomnay.com/Prod_Global/prod_global.asp).
"Parkwatch and Wherenet Unveil the First Amusement Visitor Locating system," ParkWatch, Press Release, Jun. 27, 2000, pp. 1-4.
"SnapTrack and SignalSoft Corp. Team Up to Trial Location-based Information Service for GSM Test Group," Press Release, SnapTrack Inc., Dec. 6, 1999, pp. 1-5.
"SnapTrack Awarded Additional Key Patents for Enhanced GPS System," Press Release, SnapTrack Inc., Jan. 4, 2000, pp. 1-2.
"Start-up crams single chip with phone, GPS and Bluetooth," CNET Network, Inc. (ZDNET), Mar. 22, 2002, pp. 1-2.
"The Always on Network," Position Paper, Nortel Networks, 2002, pp. 1-6.

(56) References Cited

OTHER PUBLICATIONS

"Trimble and Rosum Team to Develop Universal Positioning Technology," Trimble Navigation, Inc., News Release, Feb. 27, 2003, pp. 1-2.
"X-GPS™—Hybrid GPS Location Server Solution," Axiom Navigation Inc., 2001, 1 pg.
Commercial Uses for LoJack (webpage), LoJack Corporation, 1999, 1 pg.
Delphi and MobileAria Demonstrate True Hands Free In-Vehicle Mobile Productivity Services at CES, Press Release, Delphi Automotive Systems, Jan. 8, 2002, 3 pgs.
J.Wrolstad, "Chrysler Claims First With Bluetooth Mobile Phone System," Wireless Newsfactor, Oct. 26, 2001, 4 pgs.
K. Miyake, "Sharp to unveil 3G PDA-type cell phone," ITworld. com, Inc., Jan. 11, 2002, 2 pgs.
Kleinknecht, William, "Juvenile authorities want satellite tracking for felons," The Star-Ledger of New Jersey, Nov. 18, 1997, 4 pgs.
Marek, "The Unstoppable SnapTrack," Wireless Week, Dec. 18, 2000, Cahners Business Information, 2 pgs.
Motorola Consumer Catalog: Pagers (webpage), Motorola, Inc., 1999, 1 pg.
Ryan, "Catching up with Dick Tracy," San Francisco Chronicle, news article, Mar. 18, 2002, p. E4.
SnapTrack—Privacy Protection (webpage), SnapTrack Inc., 1998, 1 pg.
SnapTrack—Technology at Work (webpage), SnapTrack Inc., 1998, 1 pg.
SnapTrack in Action (webpage), SnapTrack Inc., 1998, 1 pg.
Stilp, Louis A., "Examining the Coming Revolution in Location Services," TruePosition, Inc., 2000, pp. 1-11.
Strom, Stephanie. "A Wild Sleigh Ride at Federal Express," The New York Times, Dec. 20, 1994, 3 pgs.
TruePosition Virtual Brochure (webpage), TruePosition, Inc. TruePosition, Inc., 2000, 2 pgs.
Wong, "Fishers, golfers join the rush to GPS," San Jose Mercury News, news article, Mar. 25, 2002, 2 pgs.
"OnGuard Tracker Nabs Auto Burglar," Section: Financial News, PR Newswire, Jul. 29, 1996, 2 pgs.
"OnGuard Tracker Makes Debut on 'One Lap of America'," PR Newswire, Jun. 7, 1996, 2 pgs.
"OnGuard Tracker Makes Debut on 'One Lap of America'," Southwest Newswire, Jun. 7, 1996, 2 pgs.
"Vehicle Navigation Units Being Measured in Luxury Autos," Global Positioning & Navigation News, vol. 6, No. 7, Apr. 4, 1996, 2 pgs.
"Advanced Business Sciences, Inc. Announces Completion of Acquisition of Comguard of Illinois," Business Wire, Aug. 26, 1998, 2 pgs.
"Advanced Business Sciences, Inc. Announces Filing With Securities and Exchange Commission," Business Wire, Jun. 25, 1999, 2 pgs.
"Advanced Business Sciences, Inc. Announces Preliminary Fourth Quarter 1998 Revenue Results," Business Wire, Feb. 4, 1999, 2 pgs.
"Company Sees Prisoner Tracking and Monitoring Market Niche," Global Positioning & Navigation News, vol. 6, No. 10, May 16, 1996, 2 pgs.
GPS-Based Personal Monitoring Systems Offered to Corrections, Private Market, Global Positioning & Navigation News, vol. 8, No. 11, Jun. 3, 1998, 3 pgs.
GPS tracks parolees, probationers, Corrections Professional, vol. 5, No. 6, Nov. 19, 1999, 1 pg.
High-Tech System Tracks Offenders—Satellites Watching Criminals, Business Wire, Nov. 14, 1997, 2 pgs.
Briefs, Global Positioning & Navigation News, vol. 9, No. 4, Feb. 24, 1999, 3 pgs.
"New Service Lets Corrections Agencies Track Offenders by Satellite," PR Newswire, Jan. 11, 1999, 2 pgs.
"New Service Lets Corrections Agencies Track Offenders by Satellite; SecurityLink Offers "GPS" Tracking for Offenders on Electronic Monitoring—Sandusky Municipal Court Adopts Technology for Local Offenders," PR Newswire, Jan. 12, 1999, 2 pgs.
"New Service Lets Corrections Agencies Track Offenders by Satellite; SecurityLink Offers 'GPS' Tracking for Offenders on Electronic Monitoring," PR Newswire, Section: Financial News, Jan. 11, 1999, 2 pgs.
"New Service Lets Corrections Agencies Track Offenders by Satellite," Satellite Today, vol. 2, No. 8, Jan. 13, 1999, 1 pg.
"Prisoner Security Monitoring Company Grabs Contracts for GPS-Based System," Global Positioning & Navigation News, vol. 7, No. 1, Jan. 15, 1997, 1 pg.
Briefs, Global Positioning & Navigation News, vol. 9, No. 3, Feb. 10, 1999, 3 pgs.
"Satellite Spotlight; Eye in the Sky to Monitor Parolees," Satellite News, vol. 21, No. 15, Apr. 13, 1998, 2 pgs.
"Satellite Spotlight: Fighting Crime From Space," Satellite News, vol. 19, No. 20, May 13, 1996, 1 pg.
"Sierra Wireless and Pro Tech Team Up on Monitoring Product," Global Positioning & Navigation News, vol. 8, No. 8, Apr. 22, 1998, 2 pgs.
Anderson, Larry, "Technology rules at Securing New Ground," Access Control & Security Systems Integration, Section: Industry Outlook; ISSN 1084-6425, Dec. 1999, 3 pgs.
Trimble Navigation Warns 2nd-Quarter Earnings to Miss Target, Dow Jones Business News, Jul. 10, 1998, 2 pgs.
"Trimble Navigation's Net Income Skidded 93% Amid Order Delays," Dow Jones Business News, Jul. 23, 1998, 2 pgs.
Briefs, Global Positioning & Navigation News, vol. 9, No. 2, Jan. 27, 1999, 3 pgs.
Briefs, Global Positioning & Navigation News, vol. 9, No. 14, Jul. 14, 1999, 3 pgs.
Zygowicz et al. "State of the Art in Automatic Vehicle Location Systems," Center for Urban Transportation Studies, University of Wisconsin, Milwaukee, Feb. 1998, pp. 1-27.
Ashworth, Jon. "Big brother is watching you," The Times (London), Section: Features, May 7, 1999, 3 pgs.
"Car Thieves Take the "Bait" in Michigan; Two Suspects Reeled in With OnGuard," Business Wire, Sep. 11, 1997, 2 pgs.
"ATX Technologies Signs Nationwide Service Deal with AT&T," Global Positioning & Navigation News, vol. 7, No. 9, May 7, 1997, 2 pgs.
"Car Thieves Take the 'Bait' in Tulsa; Two Suspects Caught Off Guard with OnGuard Once Again," PR Newswire, Section: Financial News, Jan. 8, 1997, 2 pgs.
"Car Thieves Take the 'Bait' in Tulsa; Two Suspects Caught Off Guard with on Guard," PR Newswire, Section: Financial News, Dec. 9, 1996, 2 pgs.
"San Antonio Personal Security Company Links Up with Senior Pga Golfer," PR Newswire, Section: Financial News, Apr. 1, 1996, 1 pg.
"San Antonio Personal Security Company Links Up with Senior PGA Golfer," Southwest Newswire, Apr. 1, 1996, 2 pgs.
Business Briefs, San Antonio Express-News, Mar. 25, 1996, 1 pg.
"ATX Research Signs Exclusive Sales Agreement with Arizona Company," PR Newswire, Mar. 21, 1996, 2 pgs.
"ATX Research Signs Exclusive Sales Agreement with Arizona Company, " Southwest Newswire, Mar. 21, 1996, 2 pgs.
"Automotive GPS Satellite/Safety System Race is on," Southwest Newswire, Feb. 20, 1996, 2 pgs.
"Dealerships Can Track Down New Aftermarket Revenues," PR Newswire, Feb. 9, 1996, 2 pgs.
"ATX Research Unveils New Stealthtrac Capability," PR Newswire, Feb. 9, 1996, 2 pgs.
"Dealerships Can Track Down New Aftermarket Revenues," Southwest Newswire, Feb. 9, 1996, 2 pgs.
Briefs, Global Positioning & Navigation News Wire, vol. 6, No. 2, Jan. 24, 1996, 3 pgs.
"ATX Research Provides Police Departments With Onguard Personal Security and Vehicle Tracking System," PR Newswire, Jan. 15, 1996, 2 pgs.
"ATX Research Provides Police Departments With Onguard Personal Security and Vehicle Tracking System," Southwest Newswire, Jan. 15, 1996, 2 pgs.

(56) References Cited

OTHER PUBLICATIONS

"ATX Research Relocates to New Corporate Headquarters," PR Newswire, Dec. 12, 1995, 1 pg.
"ATX Research Relocates to New Corporate Headquarters," Southwest Newswire, Dec. 12, 1995, 1 pg.
"Texas invention tracks stolen cars, lets driver call for help," The Vancouver Sun, Oct. 20, 1995, 2 pgs.
"San Antonio Company Unveils Satellite/Cellular Personal Security System," PR Newswire, Oct. 3, 1995, 3 pgs.
"San Antonio Company Unveils Satellite/Cellular Personal Security System," Southwest Newswire, Oct. 3, 1995, 3 pgs.
Moeglein, et al. "An Introduction to SnapTrack Server-Aided GPS Technology," SnapTrack Inc., pp. 1-11.
Executive Summary, Technology Systems International, Inc., pp. 1-7.
Rabinowitz and Spilker, Jr., "Positioning Using the ATSC Digital Television Signal," Rosum Corporation Whitepaper, Rosum Corporation (downloaded May 21, 2003).
SandPiper GPS Receiver, Specification sheet by Axiom Navigation Inc. (www.axiomnav.com) 2006.
Smart Antenna, Specification sheet by Axiom Navigation Inc. (www.axiomnav.com) 2008.
Swift A2 GPS Receiver, Specification sheet by Axiom Navigation Inc. (www.axiomnav.com) 2010.
Swift B2 GPS Receiver, Specification sheet by Axiom Navigation Inc. (www.axiomnav.com) 2010.
Danger Product Overview, Danger, Inc., date unknown, 5 pgs.
Bahl et al. "RADAR: An In-Building RF-based User Location and Tracking System," *Proc. of the IEEE Conf. on Comp. Comm.*, INFOCOM2000, 19$^{th}$ Annual Joint Conf. of the IEEE Computer and Communications Societies, Mar. 2000, 10 pgs.
Heinrichs et al. "Synergies in Handset Architecture," *GPS World*, Mar 2002, vol. 13, Issue 3, p. 30-39.
Hightower et al. "Location Systems for Ubiquitous Computing," *Computer*, Aug 2001, vol. 34, Issue 8, p. 57-66.
LaMance et al. "Assisted GPS," *GPS World*, Mar 2002, vol. 13, Issue 3, p. 46-51.
Palenchar, J. "E911 Update: What Major Carriers Have Planned," *Twice: This Week in Consumer Electronics*, Oct 8, 2001, vol. 16, Issue 23, p. 36.
Syrjarinne, J. "Keeping Time with Mobiles," *GPS World*, Jan. 2001, vol. 12, Issue 1, p. 22, 7pgs.
Van Diggelen et al. "Indoor GPS," *GPS World*, Sep. 2001, vol. 12, Issue 9, p. 50. 5pgs.

\* cited by examiner

LOCATION RECORD

| CURRENT | LABEL | LONG. | LAT. | TIME | DATA |
|---|---|---|---|---|---|
| 0 | Home | X1 | Y1 | 5:45 pm | 1/1/02 |
| 1 | 7 Eleven | X2 | Y2 | 5:30 pm | 1/1/02 |
| 2 | RT. 101 | X3 | Y3 | 5:15 pm | 1/1/02 |
| 3 | Work | X4 | Y4 | 5:00 pm | 1/1/02 |

HEALTH RECORD

| CURRENT | BP | HB | TEMP. | BR | DURATION |
|---|---|---|---|---|---|
| 0 | 160/85 | 70 | 98 | 15 | - |
| 1 | 180/80 | 100 | 99 | 30 | .3 |
| 2 | 160/85 | 75 | 98 | 15 | 1.1 |
| 3 | 150/90 | 60 | 98 | 10 | 8 |

ACTION RECORD

| NOTIFY | Y |
|---|---|
| ALERT | Y |
| GUIDANCE | N |
| 911 | Y |

NOTIFY RECORD

| ACTIVITY | BP | HB | TEMP. | BR |
|---|---|---|---|---|
| General | 170-199 / 70-99 | >180 <120 | 101-104 | >50 |
| Exercising | 170-199 / 70-99 | >180 <20 | 102-104 | >60 |
| Sleeping | 170-199 / 70-99 | >180 <20 | 101-104 | >50 |

ALERT RECORD ⟵ 540

| ACTIVITY | BP | HB | TEMP. | BR |
|---|---|---|---|---|
| General | 180-199 / 80-99 | 110 - 120 | 103 - 104 | >50 |
| Exercising | 180-199 / 80-99 | 180 - 200 | 103 - 104 | >60 |

FIG. 5E

GUIDANCE RECORD ⟵ 550

| ACTIVITY | BP | HB | TEMP. | BR | MSG. |
|---|---|---|---|---|---|
| General | 180-199 / 80-99 | 110 - 120 | 103 - 104 | >60 | #1 |
| Exercising | 180-199 / 80-99 | 180 - 200 | 103 - 104 | >60 | #2 |

FIG. 5F

911 RECORD

| BP | HB | TEMP. |
|---|---|---|
| >200 / >100 | >200<br><10 | >105 |

METHOD AND SYSTEM FOR PERSONALIZED MEDICAL MONITORING AND NOTIFICATIONS THEREFOR

CROSS REFERENCE TO RELATED APPLICATIONS

This application is a divisional of U.S. patent application Ser. No. 13/047,737, filed Mar. 14, 2011, now U.S. Pat. No. 8,753,273, and entitled "METHOD AND SYSTEM FOR PERSONALIZED MEDICAL MONITORING AND NOTIFICATIONS THEREFOR," which is incorporated herein by reference; which in turn is a divisional application of U.S. patent application Ser. No. 10/397,641, filed Mar. 26, 2003, now U.S. Pat. No. 7,905,832, and entitled "METHOD AND SYSTEM FOR PERSONALIZED MEDICAL MONITORING AND NOTIFICATIONS THEREFOR," which is hereby incorporated herein by reference; which in turn claims priority benefit of: (i) U.S. Provisional Patent Application No. 60/444,198, filed Jan. 30, 2003, and entitled "SYSTEM, METHOD AND APPARATUS FOR ACQUIRING, PRESENTING, MONITORING, DELIVERING, MANAGING AND USING STATUS INFORMATION," which is hereby incorporated herein by reference; (ii) U.S. Provisional Patent Application No. 60/418,491, filed Oct. 15, 2002, and entitled "SYSTEM, METHOD AND APPARATUS FOR ACQUIRING, PRESENTING, MONITORING, DELIVERING, MANAGING AND USING STATUS INFORMATION," which is hereby incorporated herein by reference; (iii) U.S. Provisional Patent Application No. 60/404,645, filed Aug. 19, 2002, and entitled "SYSTEM, METHOD AND APPARATUS FOR ACQUIRING, PRESENTING, MONITORING, DELIVERING, MANAGING AND USING POSITION AND OTHER INFORMATION," which is hereby incorporated herein by reference; and (iv) U.S. Provisional Patent Application No. 60/375,998, filed Apr. 24, 2002, and entitled "SYSTEM, METHOD AND APPARATUS FOR ACQUIRING, PRESENTING, MANAGING AND USING POSITION INFORMATION," which is hereby incorporated herein by reference.

This application is also related to: (i) U.S. patent application Ser. No. 10/397,473, filed Mar. 26, 2003, now U.S. Pat. No. 6,975,941, and entitled "METHOD AND APPARATUS FOR INTELLIGENT ACQUISITION OF POSITION INFORMATION;" (ii) U.S. patent application Ser. No. 10/397,472, filed Mar. 26, 2003, now U.S. Pat. No. 7,218,938, and entitled "METHODS AND APPARATUS TO ANALYZE AND PRESENT LOCATION INFORMATION;" (iii) U.S. patent application Ser. No. 10/397,637, filed Mar. 26, 2003, now U.S. Pat. No. 7,212,829, and entitled "METHOD AND SYSTEM FOR PROVIDING SHIPMENT TRACKING AND NOTIFICATIONS;" (iv) U.S. patent application Ser. No. 10/397,640, filed Mar. 26, 2003, now U.S. Pat. No. 7,321,774, and entitled "INEXPENSIVE POSITION SENSING DEVICE;" (v) U.S. patent application Ser. No. 10/397,474, filed Mar. 26, 2003, now U.S. Pat. No. 7,403,972, and entitled "METHOD AND SYSTEM FOR ENHANCED MESSAGING;" (vi) U.S. patent application Ser. No. 10/397,512, filed Mar. 26, 2003, and entitled "APPLICATIONS OF STATUS INFORMATION FOR INVENTORY MANAGEMENT."

BACKGROUND OF THE INVENTION

1. Field of the Invention

The present invention relates to medical condition monitoring and, more particularly, to remote monitoring of medical conditions and locations of persons.

2. Description of the Related Art

Medical conditions are often monitored for patients while admitted at a hospital or while at a doctor's office. The monitoring can assist a doctor or other medical professional in diagnosis or treatment of a patient. Typically, a specialized monitoring machine would be placed nearby the patient and then one or more sensors would be affixed to the patient. Periodically, a doctor or other medical professional would view the data output by the specialized monitoring machine. Some medical monitoring devices are portable. These portable devices permit the patient's health to be monitored over an extended period of time. A doctor or other medical professional would view the data gathered at the next visit of the patient to a hospital or doctor's office. However, typically, these medical devices, whether stationary or portable, are special purpose devices that require professionals or trained technicians to setup and use. It is unfortunate that the use of such medical devices to monitor patients outside of a hospital or doctor's office requires professional assistance and expensive equipment. These disadvantages make it impractical for widespread use of medical monitoring systems.

Thus, there is a need for improved methods and systems to facilitate personal medical monitoring.

SUMMARY OF THE INVENTION

Broadly speaking, the invention relates to improved methods and systems for personal medical monitoring. The monitoring yields status information pertaining to persons being monitored. Notifications, recommendations and/or actions can be initiated by examination or analysis of the status information.

One aspect of the invention pertains to methods and systems for monitoring status information, including health conditions, of persons. Another aspect of the invention pertains to methods and systems for providing notifications to one or more persons. The notifications can contain status information pertaining to the person being monitored. Still another aspect of the invention pertains to methods and systems for inducing an action for or on a person based on the status information of the person. Yet still another aspect of the invention pertains to methods and systems that use a web server for remote access to monitor the status of persons being monitored and/or for facilitating configuration of notifications, recommendations and/or actions to be provided. Hence, interested parties can gain access to status information pertaining to the persons being monitored via a website or, more generally, a data network (e.g., the Internet).

According to one embodiment, the status information can include health, position (location) and other information. One example of other information is environmental conditions.

The invention can be implemented in numerous ways including, a method, system, device, graphical user interface, and a computer readable medium. Several embodiments of the invention are discussed below.

As a health monitoring system, one embodiment of the invention includes at least: a plurality of medical monitoring devices affixed to persons to be monitored, the medical monitoring devices producing location information and health condition information; and a monitoring server operatively connected to the medical monitoring devices via a first network, the monitoring server receiving and storing the location information and the health condition information from the medical monitoring devices. The first network includes at least a wired network and a wireless network.

As a method for monitoring status of a person, one embodiment of the invention includes at least the acts of: acquiring status information of the person being monitored, the status information including at least health information of the person; obtaining threshold conditions to be applied; determining whether an action condition exists by comparing the health information with the threshold conditions; and initiating an action when the determining determines that the action condition exists.

As a method for monitoring status of a person, another embodiment of the invention includes at least the acts of: receiving status information of a person being monitored, the status information being provided by a status-aware mobile device affixed to the person, the status information including at least a location of the status-aware mobile device affixed to the person and a health condition of the person; determining whether a notification should be provided to the person based on at least the health condition of the person; generating a notification message based on the location and the health condition when the determining determines that a notification should be provided; and providing the notification message to the person.

Other aspects and advantages of the invention will become apparent from the following detailed description taken in conjunction with the accompanying drawings which illustrate, by way of example, the principles of the invention.

BRIEF DESCRIPTION OF THE DRAWINGS

The invention will be readily understood by the following detailed description in conjunction with the accompanying drawings, wherein like reference numerals designate like structural elements, and in which:

FIGS. 5A-5G are exemplary records of a database according to one embodiment of the invention.

DETAILED DESCRIPTION OF THE INVENTION

Figure 1:
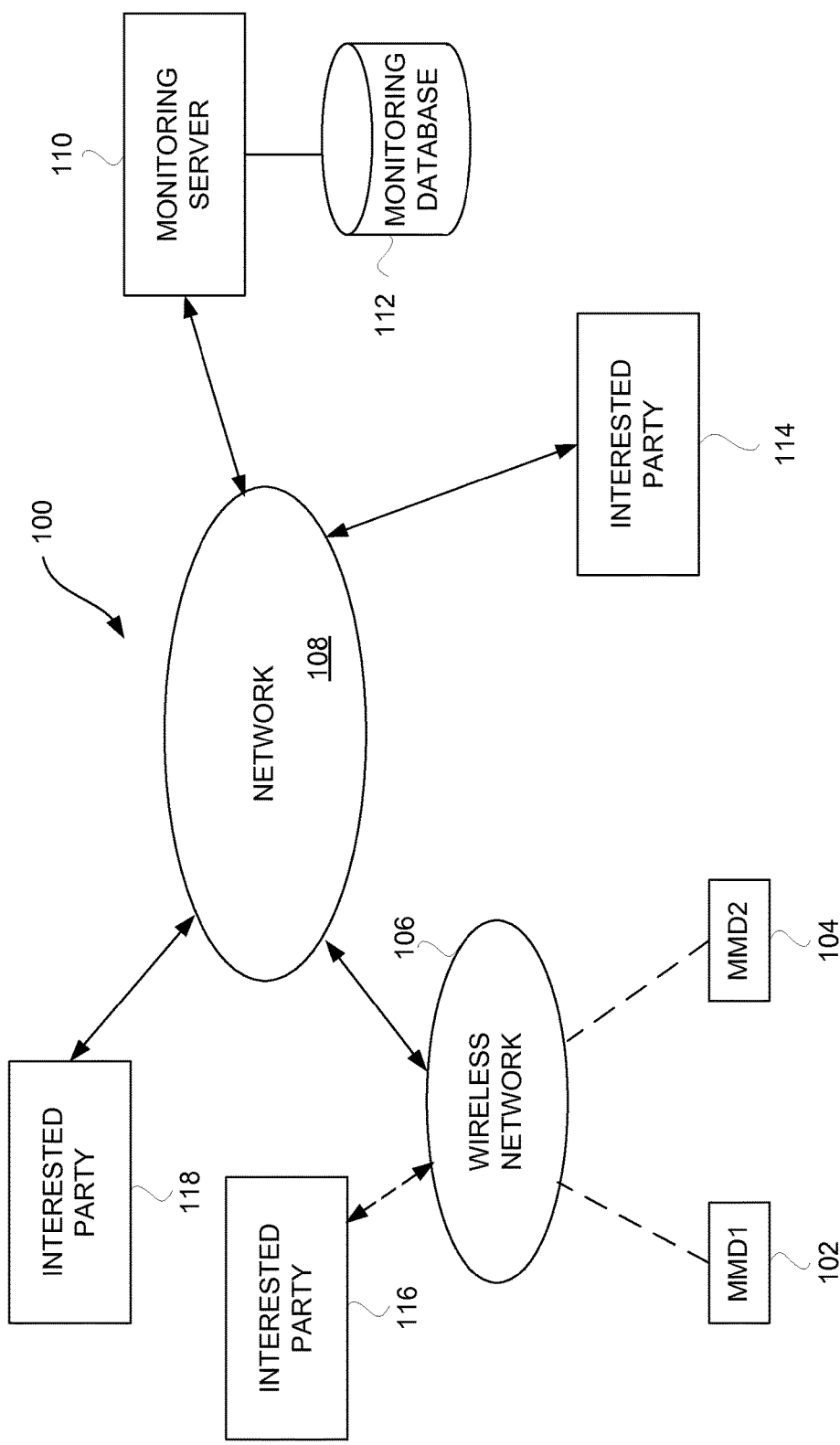
FIG. 1 is a health monitoring system according to one embodiment of the invention.

The invention relates to improved methods and systems for personal medical monitoring. The monitoring yields status information pertaining to persons being monitored. Notifications, recommendations and/or actions can be initiated by examination or analysis of the status information.

One aspect of the invention pertains to methods and systems for monitoring status information, including health conditions, of persons. Another aspect of the invention pertains to methods and systems for providing notifications to one or more persons. The notifications can contain status information pertaining to the person being monitored. Still another aspect of the invention pertains to methods and systems for inducing an action for or on a person based on the status information of the person. Yet still another aspect of the invention pertains to methods and systems that use a web server for remote access to monitor the status of persons being monitored and/or for facilitating configuration of notifications, recommendations and/or actions to be provided. Hence, interested parties can gain access to status information pertaining to the persons being monitored via a website or, more generally, a data network (e.g., the Internet).

According to one embodiment, the status information can include health, position (location) and other information. One example of other information is environmental conditions.

In the following description, numerous specific details are set forth in order to provide a thorough understanding of the present invention. However, it will become obvious to those skilled in the art that the invention may be practiced without these specific details. The description and representation herein are the common meanings used by those experienced or skilled in the art to most effectively convey the substance of their work to others skilled in the art. In other instances, well-known methods, procedures, components, and circuitry have not been described in detail to avoid unnecessarily obscuring aspects of the present invention.

Reference herein to "one embodiment" or "an embodiment" means that a particular feature, structure, or characteristic described in connection with the embodiment can be included in at least one embodiment of the invention. The appearances of the phrase "in one embodiment" in various places in the specification are not necessarily all referring to the same embodiment, nor are separate or alternative embodiments mutually exclusive of other embodiments. Further, the order of blocks in process flowcharts or diagrams representing one or more embodiments of the invention do not inherently indicate any particular order nor imply any limitations in the invention.

Embodiments of the invention are discussed below with reference to FIGS. 1-11. However, those skilled in the art will readily appreciate that the detailed description given herein with respect to these figures is for explanatory purposes as the invention extends beyond these limited embodiments.

FIG. 1 is a health monitoring system 100 according to one embodiment of the invention. The health monitoring system 100 operates to monitor health conditions or status of one or more persons. Each person having their status (e.g., health) monitored by the health monitoring system 100 has affixed thereto a medical monitoring device (MMD) 102. The medical monitoring devices 102 can be affixed to the person in a variety of ways, such as carried by the person (including carried by the person's clothing), worn by the person, located under the skin or internal to the person (i.e., in vitro or invasive to the person), etc. Examples of ways to wear such a medical monitoring device include inside a pocket of a clothing the person wears or right on the person (e.g., a piece of jewelry, watch or patch worn by the person). The medical monitoring devices 102 and 104 are described in more detail below but generally include medical sensors and communication capabilities. The medical monitoring devices 102 and 104 are coupled to a wireless network 106. In one embodiment, the wireless network 106 is a data network. For example, the data network can be a Short Message Service (SMS) network, a cellular network, a local wireless network (Bluetooth, Wi-Fi, etc.) or other wireless network. The wireless network 106 also couples to a network 108. In one embodiment, the network 108 includes at least a portion of the Internet (i.e., a global computer network). In another embodiment, the network 108 is a local area network or a wide area network. In general, the network 108 can be a wired network, a wireless network or both.

A monitoring server 110 can couple to the network 108. The monitoring server 110 can store status information (e.g., medical conditions) associated with the various persons having their status (e.g., health) being monitored by the medical monitoring devices 102 and 104. Typically, the monitoring server 110 would couple to a monitoring database 112 that stores the status information pertaining to the various users (persons). In this regard, the medical monitoring devices 102 and 104 communicate through the wireless network 106 over wireless links and can then communicate through the wireless network 106 with the monitoring server 110 via the network 108.

Additionally, an interested party 114 may also wish to interact or communicate with the medical monitoring devices 102 and 104 or the monitoring server 110. The interested party 114 is shown as being coupled to the network 108. Alternatively, an interested party 116 can also couple directly to the wireless network 106 such that the interested party 116 is able to communicate in a wireless manner either with the medical monitoring devices 102 and 104 or with the monitoring server 110 via the wireless network 106 (or some other wireless network) that couples to the network 108. Still further, an interested party 118 may also be interested in monitoring or receiving the status information pertaining to the persons having their status monitored. In one embodiment, any of the interested party 114, the interested party 116 and/or the interested party 118 can interact with the monitoring server 110 to access the status information pertaining to the persons having their status (e.g., health) monitored. In another embodiment, any of the interested party 114, the interested party 116 or the interested party 118 can interact with the monitoring server 110 to configure type, frequency and/or conditions that are to cause actions (e.g., notifications) to the interested party.

The health monitoring system 100 shown is FIG. 1 is a representative embodiment. Other embodiments of health monitoring systems can also support many medical monitoring devices, zero or more third-parties, zero or more interested parties, and zero or more monitoring servers. Also, in general, health monitoring systems can by peer-to-peer or centralized, or both. Peer-to-peer can involve status information being transmitted between medical monitoring devices, whereas centralized can involve status information being provided to a central server (e.g., monitoring server 110) and then accessible obtained from the central server.

Figure 2:
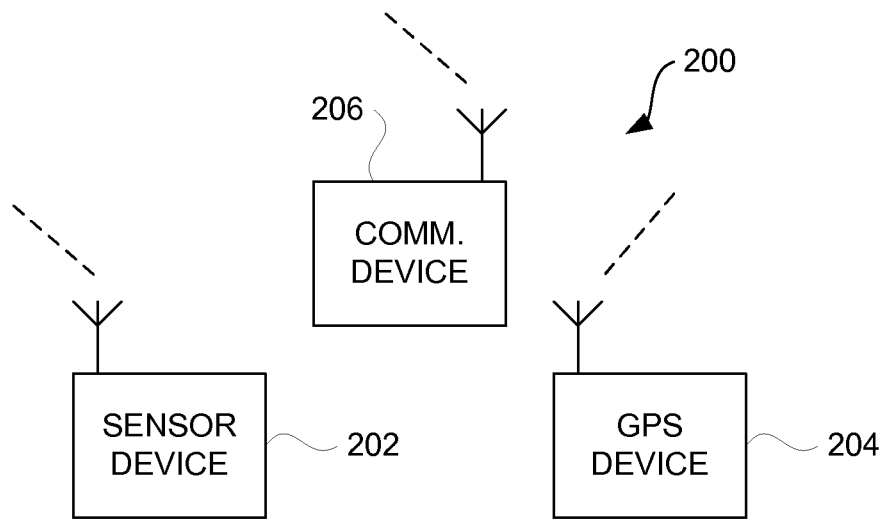
FIG. 2 is a block diagram of a medical monitoring device according to one embodiment of the invention.
Figure 3:
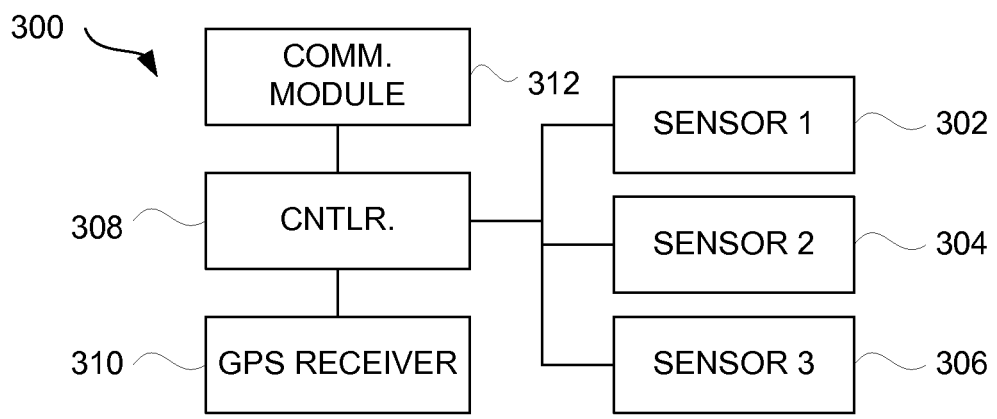
FIG. 3 is a block diagram of a medical monitoring device according to another embodiment of the invention.

Medical monitoring devices detect status information pertaining to persons, which can include health conditions. FIGS. 2 and 3 are embodiments of two representative medical monitoring devices. Additional details on medical monitoring devices can be found in U.S. Provisional Patent Application No. 60/418,491, filed Oct. 15, 2002, and entitled "SYSTEM, METHOD AND APPARATUS FOR ACQUIRING, PRESENTING, MONITORING, DELIVERING, MANAGING AND USING STATUS INFORMATION," which is hereby incorporated herein by reference.

FIG. 2 is a block diagram of a medical monitoring device 200 according to one embodiment of the invention. The medical monitoring device 200 is, for example, suitable for use as the medical monitoring device 102 or 104 illustrated in FIG. 1. The medical monitoring device 200 includes a sensor device 202, a GPS device 204, and a communication device 206. The medical monitoring device 200 is designed such that the sensor device 202 and the GPS device 204 are able to communicate with the communication device 206 in a wireless manner. The communication device 206 is then able to communicate with a wireless network (e.g., the wireless network 106) in a wireless manner. In one embodiment, the medical monitoring device 200 is worn by a person. One or more of the sensor device 202, the GPS device 204 and the communication device 206 can be provided separately. Separate devices permit flexible positioning of the devices on the person and also permit devices to be interchangeable. In one embodiment, the separate devices are each wearable by the person and communicate with one another in a wireless manner.

FIG. 3 is a block diagram of a medical monitoring device 300 according to another embodiment of the invention. The medical monitoring device 300 has an integrated design that is typically implemented as a single package. The medical monitoring device 300 can include a plurality of sensors 302, 304 and 306 that couple to a controller 308. The controller 308 can process the sensor data to the extent desired. In addition, a GPS receiver 310 can receive location data from GPS satellites and provide such location data to the controller 308. The controller 308 further controls the information about the sensor data and the location data that is communicated to the person, an interested party, or a monitoring server. When communication over a wireless link is needed, the controller 308 interacts with a communication module 312 to achieve the appropriate wireless communication.

The components can also be combined or integrated on a common integrated circuit chip to permit or facilitate sharing of some circuitry with other components or devices. For example, circuitry can be shared amongst the GPS receiver 310 and the communication module 312. As another example, circuitry can be shared amongst the sensors 302, 304 and 306. In any case, the sensors 302, 304 and 306 may couple to the person being monitored. In one embodiment, the medical monitoring device 300 is small and lightweight and thus easily wearable.

In one example, a medical monitoring device can be a mobile telephone having communication circuitry, a GPS receiver and one or more medical sensors. The sensors can be internal or external to the mobile telephone. In the case of external sensors, the sensors can couple to the mobile telephone through a wire or cable or through wireless means (e.g., Bluetooth or Wi-Fi).

Figure 4:
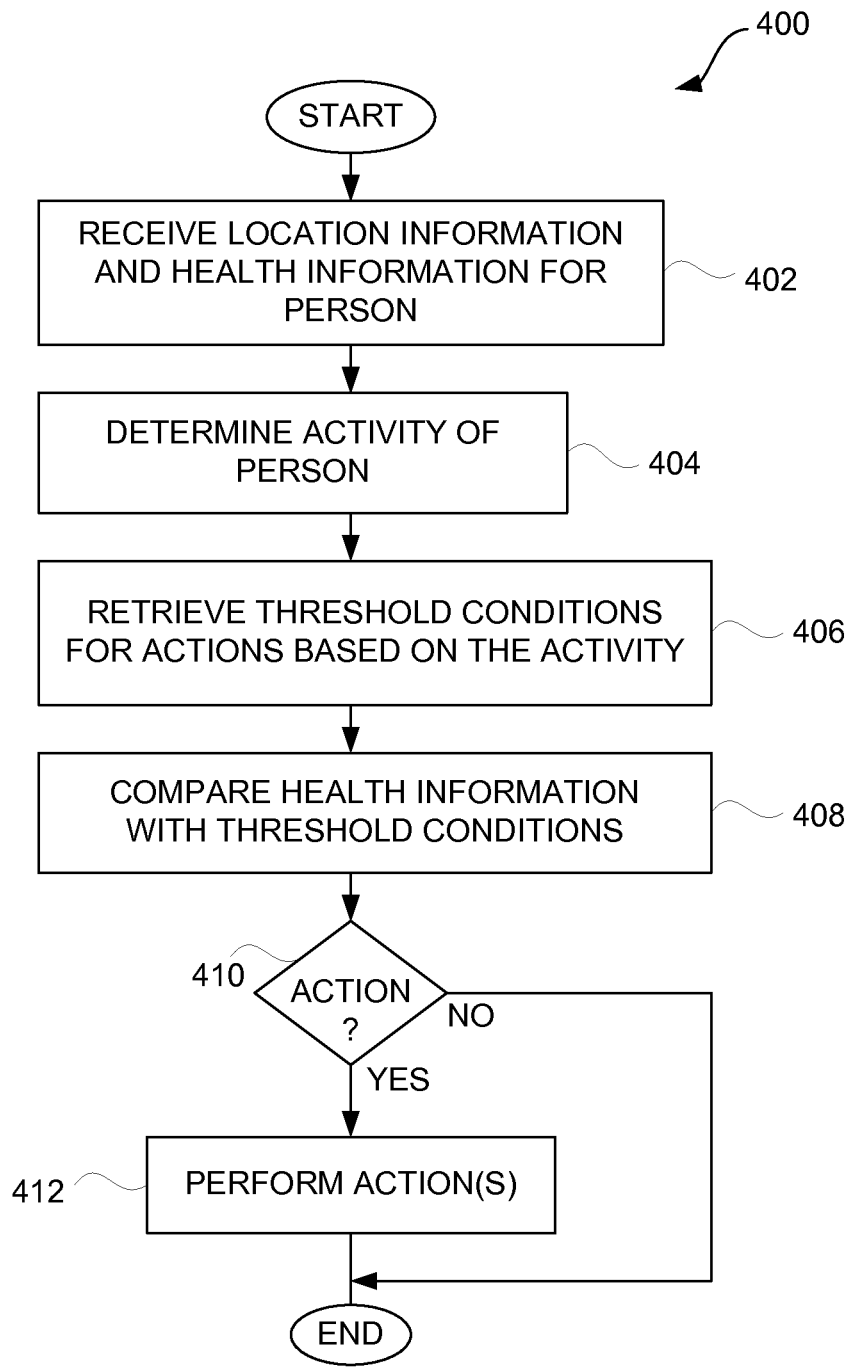
FIG. 4 is a flow diagram of an automated health processing according to one embodiment of the invention.

FIG. 4 is a flow diagram of automated health processing 400 according to one embodiment of the invention. The automated health processing 400 initially receives 402 location information and health information (medical conditions) for a person. The location information and the health information for the person are provided by a medical monitoring device. The medical monitoring device can also obtain other sensor data, such as temperature, velocity, acceleration, etc. The health information, the location information and the other sensor data can be generally considered status information.

Next, an activity of the person is determined 404. In one implementation, the activity of the person can be determined 404 based on location information and/or the other sensor data. For example, in one example, the activity of the person is distinguished between sleeping, walking, running, driving, etc. based upon velocity of movement of the person determined from a plurality of location information and/or particular sensor data. Next, threshold conditions for actions are retrieved 406 based on the activity. Note that the threshold conditions for actions can differ depending upon the activity of the person. For example, if the person is exercising, then it is expected that there should be different threshold conditions with respect to certain medical conditions, as compared to threshold conditions for use when the person is sleeping. Next, the health information is compared 408 with the threshold conditions.

A decision 410 then determines whether an action should be performed based on the result of the comparison 408. When the decision 410 determines that an action should be performed, then one or more actions are initiated 412.

The actions that can be performed 412 can vary with application. In one embodiment, the actions can include a notification or a treatment. A notification can be a message or an alert. The notifications can use any combination of text, image, audio, video or tactile action to present the notification to a user (e.g., person or interested party). In one embodiment, the notification can provide the user with information about location information and/or health information of the person. In another embodiment, the notification can provide instructions or guidance for the user. For example, the instructions or guidance can direct the person to a hospital or pharmacy and optionally also provide navigation directions. As another example, the instructions or guidance can recommend the user do certain thing to help his health condition, such as rest, take certain medicine, visit doctor, etc.

A treatment can be automatically performed on the person. In one embodiment, the medical monitoring device controls a treatment induced on the person. As examples, the treatment can automatically cause an injection of a substance to the person, release of a chemical (e.g., medicine) to the person, etc. In one embodiment, the notification and/or treatment can be dependent on one or more of the person's health conditions, the person's location, the person's activity, or the person's previous status information (e.g., health history).

Alternatively, when the decision 410 determines that no action is to be performed, then the operation 412 is bypassed. After the operation 412, or its being bypassed, the automatic health monitoring 400 is complete and ends.

The health and location information acquired by a medical monitoring device can be stored to a database, such as the monitoring database 112 illustrated in FIG. 1. Alternatively, the database could reside within a medical monitoring device or be provided elsewhere within the health monitoring system 100.

Figure 5A:

In one embodiment, each person being monitored by a medical monitoring device would have a User Identifier (UI), which can be known as a Global User Identifier (GUID). In one embodiment, the GUID can be used to link together various records within the database. For example, according to one embodiment, the records associated with a person that are stored in a database can include a location record 500 illustrated in FIG. 5A, a health record 510 illustrated in FIG. 5B, an action record 520 as illustrated in FIG. 5C, a notify record 530 as shown in FIG. 5D, an alert record 540 as shown in FIG. 5E, a guidance record 550 as shown in FIG. 5F, and a 911 record 560 as shown in FIG. 5G. The data presented in these records is merely for illustrative purposes.

The location record 500 shown in FIG. 5A can include a history of location information for the person. The location information can include a label for the location, as well as longitude and latitude data (i.e., position data) therefore. The location record 500 can also indicate time and date when the person was at the corresponding locations.

Figure 5B:
Figure 5C:
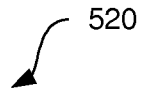
Figure 5D:
Figure 5G:

The health record 510 shown in FIG. 5B can include a history of health information, such as blood pressure (BP), heart beat (HB), and temperature (Temp.), and breathing rate per minute (BR). The health record 510 may also include duration information indicating an approximate duration (e.g., in seconds) during which the health conditions were essentially the same.

The action record 520 shown in FIG. 5C indicates the types of actions that are to be enabled. The enabled actions can then be triggered based on the health and location information retrieved from a medical monitoring device and the corresponding threshold conditions. For example, in one embodiment, the actions available for initiation or performance by a health monitoring system might include a notification, an alert, guidance or a 911 emergency call. A user, such as a system administrator or interested party, would be able to select or configure the actions to be performed for a given person being monitored.

When a notify action is to be performed, the database can include the notify record 530. The notify record 530 shown in FIG. 5D is a representative notification record which can contain threshold conditions for medical conditions to trigger notifications. Further, as shown in FIG. 5D, different sets of threshold conditions can be provided dependent upon the type of activity (e.g., general, exercising, sleeping) performed, or determined (estimated) to be performed, by the person being monitored. Typically, the notifications are to one or more interested parties. One example of a notification is an electronic mail message that contains medical condition information pertaining to the person being monitored.

The alert record 540 shown in FIG. 5E determines the threshold conditions associated with providing an alert to the person having their health and location being monitored. The alert record 540 shown in FIG. 5E is a representative alert record which can contain threshold medical conditions to trigger alerts. Different sets of threshold conditions can be provided dependent upon the type of activity performed or determined (estimated) to be performed by the person being monitored.

The guidance record 550 shown in FIG. 5F provides threshold medical conditions associated with triggering a guidance action. The guidance thresholds may be the same as the alert thresholds shown in FIG. 5E. However, the actions can be quite different. For example, an alert action can be a series of loud beeps. However, a guidance action is typically more involved. A guidance action can involve presenting one or more recommendations. The guidance action can be presented to the person by audio, graphical and/or textual means. Since the location of the person is known, the guidance can be guiding the person to a nearby pharmacy to buy a certain medicine, or to a nearby hospital to have a certain medical examination performed. Again, different threshold conditions can be provided for different activities that the person being monitored is undergoing, or for different prior medical conditions of the person.

In FIG. 5G, the 911 record 560 indicates the emergency threshold conditions for medical conditions that are used to trigger an automated 911 call. The 911 call can be an automated telephone call to a hospital, emergency response unit, (e.g., ambulance), health care provider, doctor, close relative and the like.

To trigger an action, at least one of the multiple threshold values provided in the records shown in FIGS. 5D-5G, would normally have been exceeded. In general, one or more of the thresholds can be required to be exceeded before the corresponding action is triggered.

In yet another embodiment, different threshold conditions can be set or customized based on a piece of demographic information related to the person, such as the person's ethnicity, age, gender or lifestyle. The demographic information can also include where the person resides or is presently located. For example, if the person resides or is presently located in the middle of the Sahara Desert or in the North Pole, one or more of the threshold conditions can be different.

In still another embodiment, threshold conditions can also depend on the person's prior medical conditions. More generally, different people can have same or different threshold conditions.

Although not discussed with respect to FIGS. 5A-5G, an action can include a treatment. In one embodiment, there is an additional record in the database related to the treatment performed on the person. The record can include the time, the type, and the amount of treatment administered to the person.

Still further, the database can include various other records. For example, the database could include a record that stores the status of a person when an action is initiated. As another example, a record could store the status of a person during a treatment. Still another record could archive the status of the person and actions taken.

Figure 6:
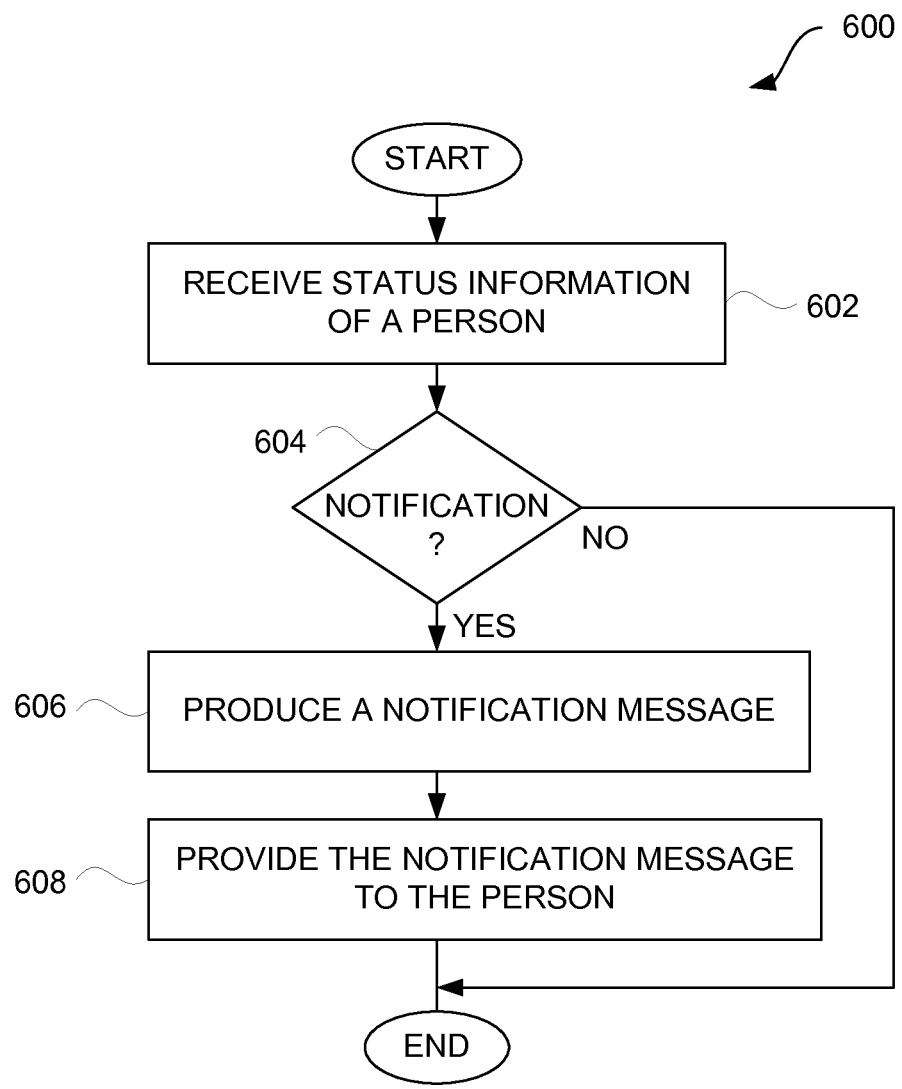
FIG. 6 is a flow diagram of personal notification processing according to one embodiment of the invention.

FIG. 6 is a flow diagram of personal notification processing 600 according to one embodiment of the invention. The personal notification processing 600 can, for example, be performed by a medical monitoring device (e.g., medical monitoring device 200, 300).

The personal notification processing 600 receives 602 status information of a person. The status information of the person can be provided by the medical monitoring device affixed to the person. A decision 604 then determines whether a notification is to be performed. The decision 604 involves an analysis of the status information of the person. Typically, the status information includes health information and location information pertaining to the person (or the medical monitoring device affixed to the person). The status information might also include environmental conditions (e.g., ambient temperature, humidity, etc.) associated with the location of the person (or the medical monitoring device). Hence, the analysis being performed determines whether the person should be notified based on the status information. In one embodiment, the health and/or location information of the status information are compared with notification criteria (e.g., threshold values). The notification criteria can, for example, be general purpose or user-specific.

The notification criteria can be set or determined in a variety of different ways. For example, the notification criteria can be dynamically determined, user-provided, or third-party provided. Typically, the determination of whether a person should be notified is based on the status information and the notification criteria. In one embodiment, the notification criteria is particular to the person being monitored. In other words, the notification criteria can be different for different persons. In another embodiment, the notification criteria can additionally or alternatively depend upon the location or activity being performed by the person.

When the decision 604 determines that no notification is to be provided, then the personal notification processing 600 is complete and ends with no notification having been performed. On the other hand, when the decision 604 determines that a notification is desired, then a notification message is produced 606.

The notification message can take a variety of different forms but generally serves to notify the person of their medical condition and/or steps to take given their medical condition. For example, the notification message can be a text message that is displayed on a small display of the medical monitoring device, a voice message that is played by the medical monitoring device, or an audio sound that is played by the medical monitoring device. After the notification message has been produced 606, the notification message is provided 608 to the person. Depending upon the type of notification message, the notification message could be provided in a different manner. For example, a text message could be provided to the person by displaying the notification message of a display of the medical monitoring device. Since the display is typically small, multiple screens or scrolling may be used to display the notification message. A voice message type notification would be provided to the person by the medical monitoring device playing the voice message. Following the operation 608, the personal notification processing 600 is complete and ends with one or more notification messages having been provided to the person. Nevertheless, the personal notification processing 600 can continue periodically, on-demand or as the status information is updated.

Figure 7:
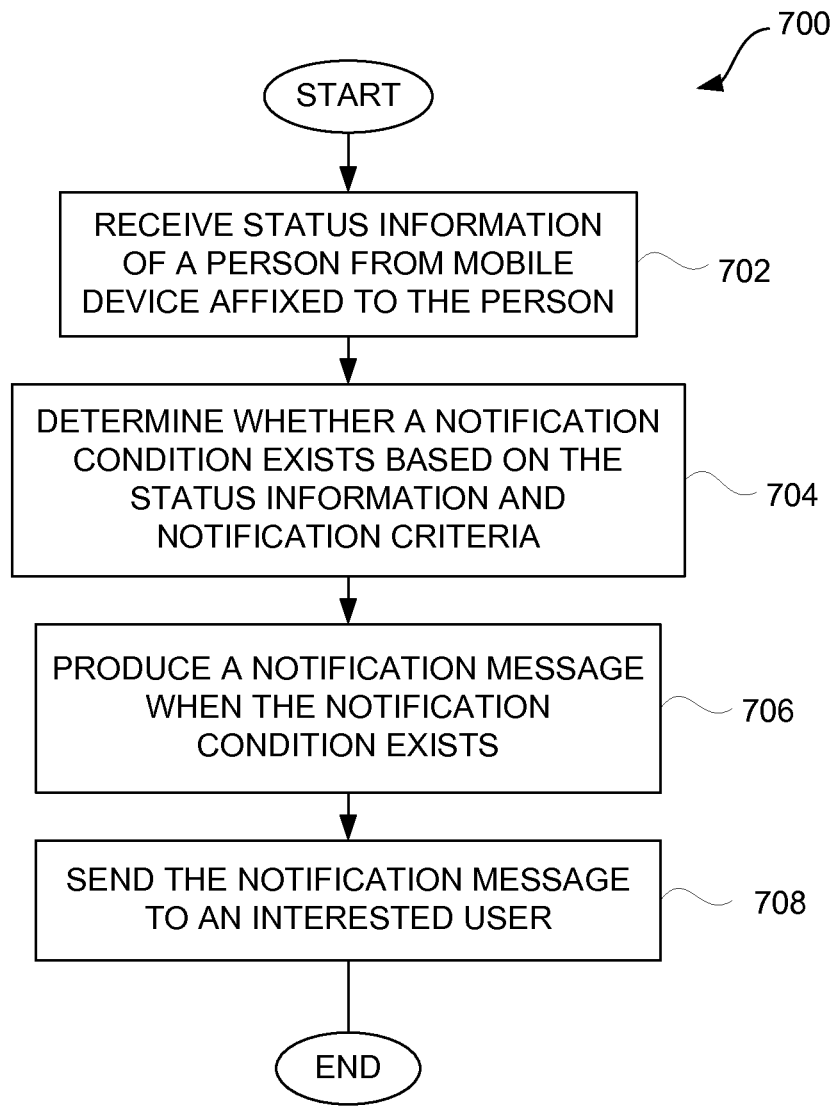
FIG. 7 is a flow diagram of remote notification processing according to one embodiment of the invention.

FIG. 7 is a flow diagram of remote notification processing 700 according to one embodiment of the invention. The remote notification processing 700 serves to notify remotely-located interested users of the health condition of a person being monitored. The remote notification processing 700 is, for example, performed by a medical monitoring device alone or with assistance with a monitoring server.

The remote notification processing 700 receives 702 status information of a person. The status information is provided by a mobile device (e.g., medical monitoring device) that is affixed to the person. Then, the remote notification processing 700 determines 704 whether a notification condition exists based on the status information and notification criteria. The notification criteria can be set or determined in a variety of different ways. For example, the notification criteria can be dynamically determined, user-provided, or third-party provided. In any case, the determination of whether a notification condition exists typically is based on the status information and the notification criteria. In one embodiment, the notification criteria are particular to the person being monitored. In other words, the notification criteria can be different for different persons. In another embodiment, the notification criteria can additionally or alternatively depend upon the location or activity being performed by the person.

Thereafter, assuming a notification condition does exist, a notification message is produced 706. As noted above, the notification message can be of a variety of different types, including text, voice and audio. After the notification message has been produced 706, the notification message is sent 708 to an interested user. An interested user can be anyone desirous of receiving notification messages pertaining to the status of the person being monitored. Here, the notification message is sent to a wireless and/or wired network to a device associated with the interested user. For example, when the notification message is an electronic mail message, the electronic mail message can be transmitted through a wired or wireless network to a communication or computing device associated with the interested user. The interested user is then able to receive and read the electronic mail message and thus being informed of the health condition of the person being monitored. Similarly, the notification message might be a voice message that is transmitted to the interested user. Regardless of the type of notification message, although not shown in FIG. 7, the remote notification processing 700 could verify that the interested user is authorized to receive such a notification message before the notification message is sent 708 to the interested user. After the notification message has been sent 708 to the interested user, the remote notification processing 700 is complete and ends. Nevertheless, the remote notification processing 700 can continue periodically, on-demand or as the status information is updated.

Figure 8:
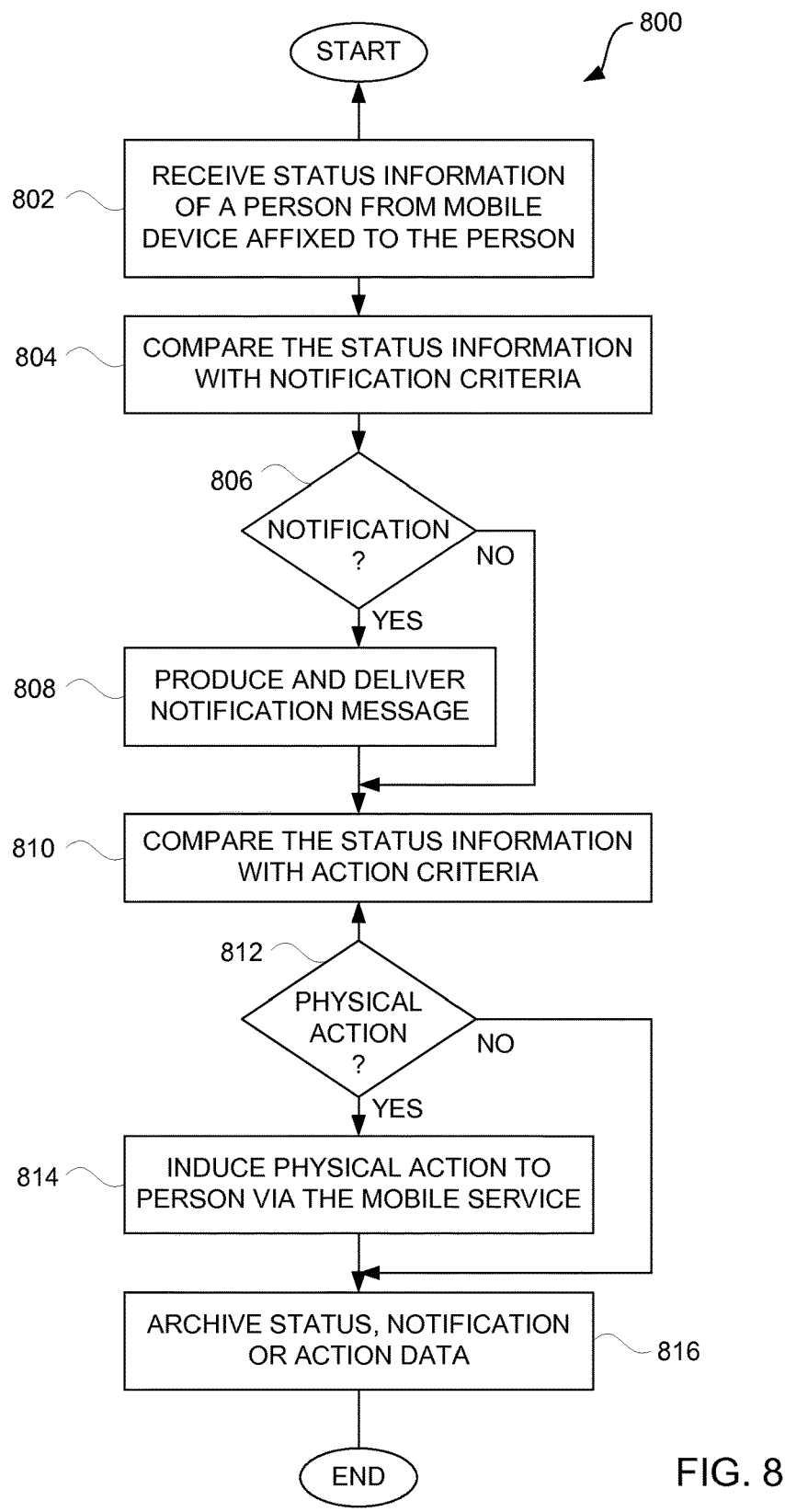
FIG. 8 is a flow diagram of notification and physical response processing according to one embodiment of the invention.

FIG. 8 is a flow diagram of notification and physical response processing 800 according to one embodiment of the invention. The notification and physical response processing 800 is, for example, performed by a medical monitoring device alone or with the assistance of a monitoring server.

The notification and physical response processing 800 receives 802 status information of a person. Typically, the status information of the person is provided by a medical monitoring device (affixed or coupled to the person). The status information that has been received 802 is then compared 804 with notification criteria. Here, according to one embodiment, the notification criteria can be specific to the person and/or can depend upon status information. In one embodiment, the particular notification criteria utilized is dependent upon the person and may be further dependent on the status information (e.g., type of status information). Next, a decision 806 determines whether a notification is needed. When the decision 806 determines that a notification is needed, then a notification message is produced and delivered 808. Alternatively, when the decision 806 determines that a notification is not needed, then the operation 808 is bypassed.

Besides the notification, the notification and physical response processing 800 can also induce a physical response to the person. Typically, the physical response would be induced to the person by the medical monitoring device affixed to the person. In this regard, the status information for the person is compared 810 with action criteria. Here, according to one embodiment, the action criteria can be specific to the person and/or can depend upon status information. The comparison 810 of the status information with the action criteria can also take into account a history of the status information for the person.

Next, a decision 812 determines whether a physical action should be induced. When the decision 812 determines that a physical action should be induced based on the comparison 810, then a physical action is induced 814 to the person via a device, which can be a mobile device. The type of physical action that is induced 814 can depend upon the capabilities of the mobile device. Examples of physical actions that can be induced 814 include introduction of insulin, drugs, and the like to the person. The introduction may be achieved through a needle, a patch, a device fabricated by micromachining techniques, and various others.

The physical actions can, for example, administer a dosage of medication to a person, such as performed through an actuator. This actuator can be a Micro-Electro-Mechanical System (MEMS) device fabricated using micromachining techniques. One advantage of a MEMS device is that the amount of dosage can be minute and automated. In one embodiment, the medical monitoring device can also simultaneously sense the status of the person while administering a small amount of medication. The medical monitoring device with an actuator can introduce (e.g., inject) an accurate amount of medication into the person. The amount introduced can depend on the medical condition as well as activity level of the person. The amount introduced can be furthered modified in view of the person's medical history. Since the dosage can be minute, and its effect simultaneously monitored, the possibility of over-dosage can be significantly decreased. As an example, a diabetic person could use a medical monitoring device with an actuator. The medical monitoring device senses a blood sugar level of the diabetic person, and introduces (e.g., injects) a controlled amount of insulin into the diabetic person's blood stream to stabilize it. The medical monitoring device can further determine the diabetic person's activity level and adjust the amount of insulin accordingly. In one embodiment, at least a portion of the medical monitoring device is attached to the person to be monitored (e.g., attached to the arm of the person, embedded within the person's body, etc.).

Alternatively, when the decision 812 determines that a physical action is not to be induced, then the operation 814 is bypassed. Following the operation 814 or its being bypassed, if desired, the notification and physical response processing 800 can archive 816 status, notification or action data such that subsequent analysis of the data can be performed. Also, the history of the medical condition and actions taken can be archived for later review. Following the operation 816, the notification and physical response processing 800 is complete and ends. Nevertheless, the notification and physical response processing 800 can continue periodically, on-demand or as the status information is updated.

Figure 9:
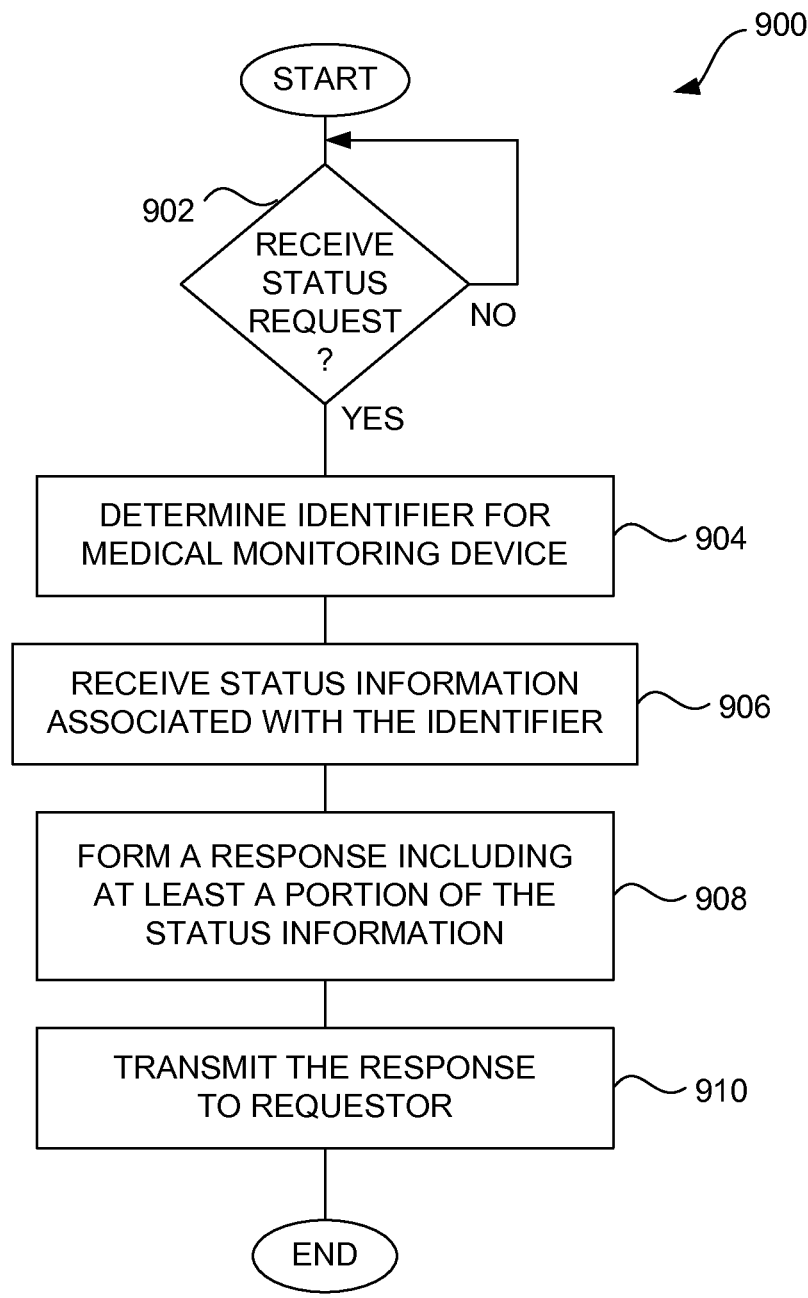
FIG. 9 is a flow diagram of requested notification processing according to one embodiment of the invention.

FIG. 9 is a flow diagram of requested notification processing 900 according to one embodiment of the invention. The requested notification processing 900 is, for example, performed by a server machine, such as the monitoring server 110 illustrated in FIG. 1.

The requested notification processing 900 begins with a decision 902 that determines whether a status request has been received. When the decision 902 determines that a status request has not been received, the requested notification processing 900 awaits such a request. In other words, the requested notification processing 900 can be considered to be invoked when a status request is received. A user (i.e., requestor) typically initiates the requested notification processing 900 when status information is desired by making a status request (or notification request). Typically, the user makes a status request by use of a client device associated with the user (i.e., requestor).

Once the decision 902 determines that a status request has been received, then an identifier for a medical monitoring device is determined 904. The identifier serves to identify the particular medical monitoring device for which the status information is to be obtained. After the identifier is identified, status information for the medical monitoring device associated with the identifier is retrieved 906. If desired, the requested notification processing 900 can further determine whether the requestor for the status information is authorized to receive the status information.

After the status information has been retrieved 906, a response including at least a portion of the status information is formed 908. In one embodiment, the response being formed 908 is in the format of an electronic mail (email)

message (including any text or graphical message being electronically transmitted). For example, if the status request were in the form of an email message (including any text or graphical message being electronically transmitted), the response could be a reply email to the status request email message. In one implementation, the email message is an instant message, namely a near real time text message. In other embodiments, the response being formed 908 can take various other formats. After the response has been formed 908, the response is transmitted 910 to the requestor. The transmission of the response can be over a wireless and/or a wired network. For example, when the format of the response is an email message, the response is typically sent to a network address or email address associated with the requestor that issued the status request. Following the operation 910, the requested notification processing 900 is complete and ends.

Figure 10:
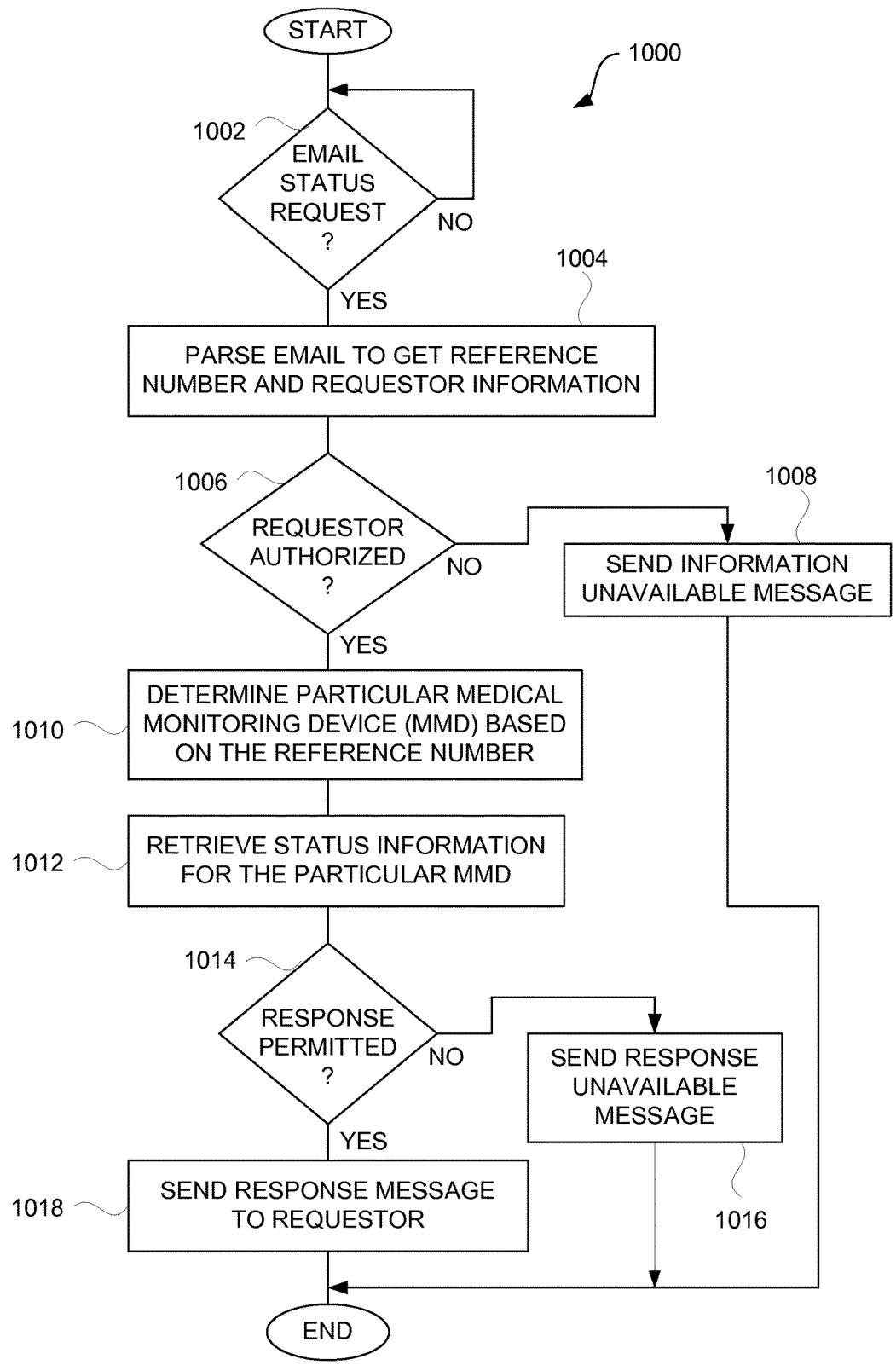
FIG. 10 is a flow diagram of email status processing according to one embodiment of the invention.

FIG. 10 is a flow diagram of email status processing 1000 according to one embodiment of the invention. The email status processing 1000 is, for example, performed by a server machine, such as the monitoring server 110 illustrated in FIG. 1. The email status processing 1000 can be considered a more detailed embodiment of the requested notification processing 900 illustrated in FIG. 9.

The email status processing 1000 begins with a decision 1002 that determines whether an email status request has been received 1002 from a requestor. When the decision 1002 determines that an email status request has not been received, then the email status processing 1000 awaits such a request. Once the decision 1002 determines that an email status request has been received, then the email status request can be parsed 1004 to get a reference number and requestor information.

Next, a decision 1006 determines whether the requestor is authorized. Here, the determination of whether or not the requestor is authorized can be performed using some or all of the requestor information and the reference number for the medical monitoring device of interest. When the decision 1006 determines that the requestor is not authorized, then an information unavailable message is sent 1008 to the requestor.

When the decision 1006 determines that the requestor is authorized, the medical monitoring device is determined 1010 based on the reference number. As an example, the reference number can be an identifier that is used by users to identify the medical monitoring device they are desirous of tracking. Internally the system may use the reference number or another identifier. The reference number may be a fixed number or a re-assignable number that specifies a particular medical monitoring device. For example, the reference number can be a telephone number or network address used by the medical monitoring device for communications.

After the medical monitoring device has been determined 1010, the status information for the determined medical monitoring device is retrieved 1012. In one embodiment, the status information is retrieved 1012 from a database that stores status information for a plurality of medical monitoring devices or the persons having the medical monitoring devices affixed thereto. The database is, for example, the tracking database 116 illustrated in FIG. 1.

Next, a decision 1014 determines whether the requested response is permitted. In other words, although the requestor is permitted to access the status information, the type (e.g., format or content) of response that is permitted to be supplied to the requestor could be limited. Hence, when the decision 1014 determines that the requested response is not permitted, then a requested response unavailable message is sent 1016 to the requestor. On the other hand, when the decision 1014 determines that the requested response is permitted, then a response message is produced and sent 1018 to the requestor. In one embodiment, the message can take different formats or content depending upon a user's configuration request, a requestor's authorization level, or the destination for the response message. Following the operation 1018, as well as following the operations 1008 and 1016, the email status processing 1000 ends.

A web interface (or Graphical User Interface) can be made available to users. The web interface can, among other things, assist a user with configuring notifications for themselves or others. One embodiment of such a web interface is referred to as a notification setup screen. A web interface could also be used to allow a requestor to view requested status information.

The position resolution can be enhanced through use of a community layout and/or localized profile information.

Figure 11:
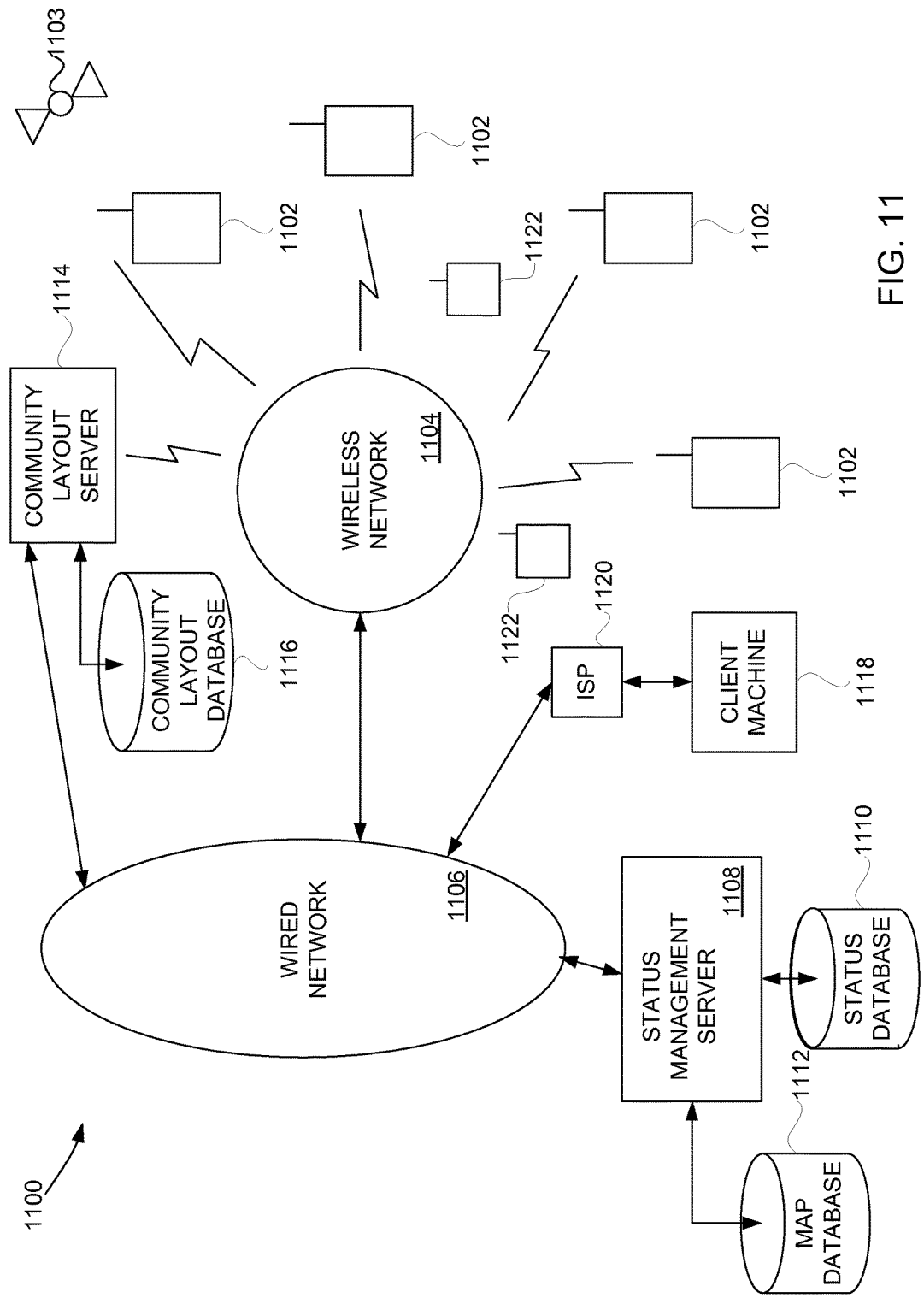
FIG. 11 is a block diagram of an object monitoring system according to one embodiment of the invention.

FIG. 11 is a block diagram of a monitoring system 1100 according to one embodiment of the invention. The monitoring system 1100 can be used to monitor medical conditions of beings, such as humans and/or pets (users). The monitoring system 1100 includes a plurality of mobile devices 1102. These mobile devices 1102 are provided with, affixed to or proximate to users being tracked by the monitoring system 1100. These mobile devices 1102 can have GPS receivers that can receive GPS position information from a GPS system 1103. The mobile devices 1102 also receive health information from sensors as noted above for medical monitoring devices. The acquisition of such position or health information can be performed on demand, periodically or on need. The mobile devices 1102 communicate over wireless links with a wireless network 1104. The wireless network 1104 then couples to a wired network 1106. A status management server 1108 is coupled to the wireless network 1106. The status management server 1108 provides centralized storage of status information (e.g., health information, location information and possibly other information) for each of the mobile devices 1102 or its users in a status database 1110. A map database 1112 is also coupled to the status management server 1108. The map database 1112 can directly connect to the status management server 1108 or can reside elsewhere on the wired network 1106. The status management server 1108 can interact with the map database 1112 to convert position information provided by the GPS information into map coordinates, street addresses, etc.

In addition, the object monitoring system 1100 also includes a community layout server 1114. The community layout server 1114 can be coupled to the wired network 1106 or the wireless network 1104. In one embodiment, a community can be associated with a commercial building, a shopping mall, a residential community and the like. The community layout server 1114 interacts with a community layout database 1116 to resolve locations, such as street addresses, cross streets or longitude and latitude, into precise locations in a community. For example, the precise locations can pertain to points of interest with respect to the community. As an illustration, in the case of a commercial building, with five floors, the community layout database 1116 would convert the GPS information (plus any additional sensor information relevant to making the determination may also be provided by the mobile device 1102, such as altitude and direction) to obtain a community location or point of interest. For example, using the GPS position information together with other sensor information, the community layout server 1114 can interact with the community layout database 1116 to precisely locate a particular mobile device 1102 to a particular point of interest. For example, in the case of the commercial building with five floors, the mobile device 1102 can be pinpointed to the third floor which pertains to the corporation Acme, Inc. The point of interest or community position can then be sent from the community layout server 1114 through the wired network 1106 to the location management server 1108 which then in turn stores the community position or point of interest in the status database 1110 as the position of the particular mobile device 1102.

Once the status database 1110 has the positions of the mobile devices 1102, when subsequent position data is sent to the status management server 1108, these positions are suitably updated in the status database 1110. Additionally, other of the mobile devices 1102 or a representative client machine 1118 coupled through an Internet Service Provider (ISP) 1120 to the wired network 1106 can be permitted to access the status of one or more of the mobile devices 1102. Assuming that the requesting party is allowed access to status information, the request for such information is processed by the status management server 1108. When permission is granted, the status desired is retrieved from the status database 1110 and returned to either the requesting mobile devices 1102 or the requesting client machine 1118.

In one embodiment, the client machine 1118 or a particular one of the mobile devices 1102, or users thereof, can set up a private or semi-private web page that is hosted by a server (e.g., the status management server 1108 or other server) on the wired network 1106. Then, the page can be customized to monitor the status of a number of the mobile devices 1102 (namely, the persons affixed thereto). Hence, thereafter, the requestor need only access the customized web page to obtain the current status information for such mobile devices. With such an embodiment, a web page could be provided to monitor one or more persons. In another embodiment, a similar web page can be setup to allow a user to track the status of mobile devices that are affixed to, for example, his elderly parents. This would allow the requestor (interested person) to easily monitor the status (e.g., medical information and/or location information) of, for example, his parents.

The monitoring system 1100 could also be augmented by wireless profile devices 1122. These profile devices 1122 can wirelessly couple to the mobile devices 1102 using the wireless network 1104. The profile devices 1122 could be short range transmitters or transceivers. The profile devices 1122 could store one or more profiles for a particular location in which they reside.

Hence, the mobile device 1102 can wirelessly communicate with the profile device 1122, if available, to acquire a profile pertaining to its location. For example, with the profile device 1122 placed in the office building of Acme, Inc., when the mobile device 1102 is in such office building, the mobile device 1102 can acquire the profile from the profile device 1122 that is proximate to the mobile device 1102. The profile can include the business name, its location, contact information for the business, etc. Thereafter, some or all of the profile information can be stored in the mobile device 1102 and/or forwarded to the status management server 1108 or other server for storage. Hence, the location provided by the profile may be more exacting and descriptive than the GPS position, such that the location of the mobile device 1102 can be better determined.

In some cases it may be useful to control or limit the wireless communications with respect to the profile devices 1122 so that the mobile devices 1102 do not inadvertently receive the wrong profile. Various techniques can be utilized to provide control over the wireless communications. For example, the profile device 1122 may or may not use a directional antenna. As another example, the profile device 1122 could also control (e.g., limit) its transmission power so that its profile information can only be received by devices within a certain distance.

In still another embodiment, personalized medical monitoring can be provided. For example, a user can monitor themselves or a user can monitor another person as they desire. Such monitoring can be achieved independent of a medical facility.

A representative scenario is as follows. A user acquires a status-aware mobile communication device, such as a medical monitoring device, and affixes the mobile communication device to the person to be monitored. The user makes note of the identifier for the mobile communication device and the person being monitor. Then, periodically or on-demand, the user can determine the status of the monitored person. In one implementation, the user (or a server on the user's behalf) sends a message to the mobile communication device. The message can be a voice or text message that simply requests the mobile communication device to get its present status. The mobile communication device then determines status data being requested. The request can be for the health condition of the person being monitored through use of sensors of the mobile communication device. The mobile communication device can determine its location, for example, by directly using a GPS receiver or indirectly via a hub device having GPS awareness. Further, battery lifetime can be conserved using the intelligent GPS information acquisition approaches as, for example, noted in U.S. Provisional Patent Application No. 60/375,998. The mobile communication device then replies back (e.g., through voice or text message) to the user (or server) to inform of the status of the monitored person. The user can, for example, call or page the mobile communication device and get the status data in a reply message. Alternatively, the user needs only access a server to retrieve the status data it holds for the person being monitored. The server can also automatically monitor these mobile communication devices and notify or alert users (e.g., the monitored person or interested party) when problems or dangerous conditions are identified. Besides health conditions and location, reply messages could also provide other information back such as velocity, temperature, humidity, pressure, forces or stresses.

In one embodiment, the mobile device (mobile communication device) can include a solar panel. The solar panel can provide electrical power for the mobile device. The solar panel can thus charge a battery used to power the mobile device and/or itself power the mobile device. When the mobile device is affixed to a person to be monitored, the solar panel can remain at least partially exposed to the outside environment so as to be able to receive light. The solar panel can be integrated with the housing of the mobile device or can be separate and coupled to the mobile device via one or more wires (e.g., a cable).

The present invention has described one or more GPS devices as to identify a location. However, the present invention is not limited to using GPS devices. In certain situations, other wireless or mobile devices can also serve as location-designating devices, such as devices based on GSM technologies, Bluetooth or Wi-Fi technologies. Through the techniques of triangulation, these devices can also designate a location. Such triangulation techniques should be known to those skilled in the art.

Although the invention has been described above in the context of monitoring persons, the invention can likewise be used to monitor animals (e.g., pets) or other living beings.

The above-described systems, devices, methods and processes can be used together with other aspects of a monitoring system, including the various aspects described in: (i) U.S. Provisional Patent Application No. 60/444,198, filed Jan. 30, 2003, and entitled "SYSTEM, METHOD AND APPARATUS FOR ACQUIRING, PRESENTING, MONITORING, DELIVERING, MANAGING AND USING STATUS INFORMATION," which is hereby incorporated herein by reference; (ii) U.S. Provisional Patent Application No. 60/418,491, filed Oct. 15, 2002, and entitled "SYSTEM, METHOD AND APPARATUS FOR ACQUIRING, PRESENTING, MONITORING, DELIVERING, MANAGING AND USING STATUS INFORMATION," which is hereby incorporated herein by reference; (iii) U.S. Provisional Patent Application No. 60/404,645, filed Aug. 19, 2002, and entitled "SYSTEM, METHOD AND APPARATUS FOR ACQUIRING, PRESENTING, MONITORING, DELIVERING, MANAGING AND USING POSITION AND OTHER INFORMATION," which is hereby incorporated herein by reference; and (iv) U.S. Provisional Patent Application No. 60/375,998, filed Apr. 24, 2002, and entitled "SYSTEM, METHOD AND APPARATUS FOR ACQUIRING, PRESENTING, MANAGING AND USING POSITION INFORMATION," which is hereby incorporated herein by reference.

The various embodiments, implementations and features of the invention noted above can be combined in various ways or used separately. Those skilled in the art will understand from the description that the invention can be equally applied to or used in other various different settings with respect to various combinations, embodiments, implementations or features provided in the description herein.

The invention can be implemented in software, hardware or a combination of hardware and software. The invention can also be embodied as computer readable code on a computer readable medium. The computer readable medium is any data storage device that can store data which can thereafter be read by a computer system. Examples of the computer readable medium include read-only memory, random-access memory, CD-ROMs, magnetic tape, optical data storage devices, and carrier waves. The computer readable medium can also be distributed over network-coupled computer systems so that the computer readable code is stored and executed in a distributed fashion.

The advantages of the invention are numerous. Different embodiments or implementations may yield different advantages. One advantage of the invention is that a person's health can be monitored with a portable medical monitoring system. Another advantage of the invention is that portable medical monitoring systems can be low cost and utilized without assistance of medical professionals or trained technicians. Still another advantage of the invention is that status information of a person being monitored can be obtained by an interested party through notifications or through access to a website (e.g., monitoring server). Yet another advantage of the invention is that notifications, recommendations and/or actions can be initiated by examination or analysis of the status information.

The many features and advantages of the present invention are apparent from the written description and, thus, it is intended by the appended claims to cover all such features and advantages of the invention. Further, since numerous modifications and changes will readily occur to those skilled in the art, it is not desired to limit the invention to the exact construction and operation as illustrated and described. Hence, all suitable modifications and equivalents may be resorted to as falling within the scope of the invention.

The invention claimed is:

1. A health monitoring system, comprising:
a plurality of medical monitoring devices configured to be affixed to persons to be monitored, said medical monitoring devices configured to obtain location information and health condition information; and
a monitoring server operatively connected to said medical monitoring devices via one or more networks, said monitoring server configured to receive and store the location information and the health condition information from said medical monitoring devices,
wherein the one or more networks includes at least a wired network and a wireless network,
wherein, for at least one of said medical monitoring devices, said monitoring server is configured to determine whether one or more notifications are to be sent to at least one recipient based on at least a portion of the health condition information received from one or more of said medical monitoring devices,
wherein said monitoring server is configured to initiate sending of the one or more notifications to the at least one recipient when said monitoring server determines that the one or more notifications are to be sent to at least one recipient based on at least a portion of the health condition information received from one or more of said medical monitoring devices, and
wherein said monitoring server is configured to provide a web interface that is accessed by at least one potential recipient to configure when and where the one or more notifications are to be sent, the web interface enabling the at least one potential recipient to designate the sending of the one or more notifications to the at least one potential recipient in a manner that is at least partially dependent on the location information.

2. The health monitoring system as recited in claim 1, wherein each of said plurality of medical monitoring devices comprises at least one medical sensor configured to acquire the health condition information pertaining to the person corresponding thereto.

3. The health monitoring system as recited in claim 1, wherein the at least one recipient is one of the persons or an interested party.

4. The health monitoring system as recited in claim 1, wherein the one or more notifications are electronic mail messages.

5. The health monitoring system as recited in claim 1, wherein each of said plurality of medical monitoring devices comprises:
a wireless communication component configured to communicate over the one or more networks;
a GPS component configured to acquire the location information corresponding thereto; and
at least one medical sensor configured to acquire the health condition information pertaining to the person corresponding thereto.

6. The health monitoring system as recited in claim 5, wherein said wireless communication component, said GPS component and said at least one medical sensor are integrated into a single package.

7. The health monitoring system as recited in claim 5,
wherein said wireless communication component is provided in a first apparatus,
wherein said GPS component and said at least one medical sensor are provided in a second apparatus, and wherein the second apparatus is configured to communicate with said wireless communication component through a wireless local network, and said wireless communication component is configured to communicate with said monitoring server over the one or more networks.

8. The health monitoring system as recited in claim 7, wherein the wireless local network is a Wi-Fi wireless network.

9. The health monitoring system as recited in claim 5,
wherein said wireless communication component is provided in a first apparatus,
wherein said at least one medical sensor is provided in a second apparatus, and
wherein the second apparatus is configured to communicate with said wireless communication device through a wireless local network, and said wireless communication device is configured to communicate with said monitoring server over the one or more networks.

10. The health monitoring system as recited in claim 5, wherein the web interface is further configured to denote how the one or more notifications are to be sent.

11. A health monitoring system, said health monitoring system supporting a plurality of medical monitoring devices, the medical monitoring devices being configured to be carried or worn by persons to be monitored, the medical monitoring devices being configured to obtain location information and health condition information pertaining to the persons, said health monitoring system comprising:
a monitoring server operatively connected to the medical monitoring devices via one or more networks, said monitoring server configured to receive and store the location information and the health condition information from the medical monitoring devices,
wherein, for at least one of the medical monitoring devices, said monitoring server is configured to determine whether one or more electronic notifications are to be sent to at least one recipient based on at least a portion of the health condition information received from one or more of the medical monitoring devices and based on criteria for when the one or more electronic notifications are to be sent,
wherein said monitoring server is configured to initiate sending of the one or more electronic notifications to the at least one recipient when said monitoring server determines that the one or more electronic notifications are to be sent to at least one recipient based on at least a portion of the health condition information received from one or more of the medical monitoring devices and based on criteria for when the one or more electronic notifications are to be sent, and
wherein said monitoring server is configured to provide a web interface that is accessed by at least one potential recipient to configure the criteria for when the one or more electronic notifications are to be sent to the at least one recipient.

12. The health monitoring system as recited in claim 11, wherein the criteria for when the one or more electronic notifications are to be sent are at least partially dependent on the location information pertaining to the persons.

13. The health monitoring system as recited in claim 11, wherein the web interface that is accessed by at least one potential recipient further permits the at least one potential recipient to configure information as to where the one or more electronic notifications for the at least one potential recipient are to be sent.

14. The health monitoring system as recited in claim 13, wherein the criteria for when the one or more electronic notifications are to be sent are at least partially dependent on the location information pertaining to the persons.

15. The health monitoring system as recited in claim 11, wherein each of the plurality of medical monitoring devices comprises at least one medical sensor configured to acquire the health condition information pertaining to the person corresponding thereto.

16. The health monitoring system as recited in claim 11, wherein the one or more notifications are electronic text messages.

17. The health monitoring system as recited in claim 11, wherein each of the plurality of medical monitoring devices comprises:
a wireless communication component configured to communicate over the one or more networks;
a GPS component configured to acquire the location information corresponding thereto; and
at least one medical sensor configured to acquire the health condition information pertaining to the person corresponding thereto.

18. The health monitoring system as recited in claim 17, wherein the wireless communication component, the GPS component and the at least one medical sensor are integrated into a single package.

19. The health monitoring system as recited in claim 17,
wherein the wireless communication component is provided in a first apparatus,
wherein the GPS component and/or the at least one medical sensor as provided in a second apparatus, and
wherein the second apparatus is configured to communicate with the wireless communication component through a wireless local network, and the wireless communication component is configured to communicate with the monitoring server over the one or more networks.

20. The health monitoring system as recited in claim 11,
wherein at least one of the medical monitoring devices includes a capability to induce an action to the person carrying or wearing the at least one of the medical monitoring devices, and
wherein said monitoring server is configured to determine when to induce an action to the person carrying or wearing the at least one of the medical monitoring devices based on at least a portion of the health condition information received from the at least one of the medical monitoring devices and based on criteria for when an action is to be induced.

21. The health monitoring system as recited in claim 11, wherein the one or more notifications are electronic audio and/or graphical messages.

22. The health monitoring system as recited in claim 18, wherein the criteria for when the one or more electronic notifications are to be sent are at least partially dependent on the location information pertaining to the person.

23. The health monitoring system as recited in claim 12, wherein the web interface that is accessed by at least one potential recipient further permits the at least one potential recipient to configure information as to where the one or more electronic notification for the at least one potential recipient are to be sent.

24. The health monitoring system as recited in claim 18, wherein the one or more notifications are electronic text messages.

25. The health monitoring system as recited in claim 11, wherein the one or more notifications are electronic audio and/or graphical messages.

26. The health monitoring system as recited in claim 11, wherein the recipient is the person.

* * * * *